US007087607B2

(12) United States Patent
Gerlach et al.

(10) Patent No.: US 7,087,607 B2
(45) Date of Patent: Aug. 8, 2006

(54) SALTS OF BICYCLIC, N-ACYLATED IMIDAZO-3-AMINES AND IMIDAZO-5-AMINES

(75) Inventors: Matthias Gerlach, Brachttal (DE); Corinna Sundermann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 169 days.

(21) Appl. No.: 10/273,344

(22) Filed: Oct. 18, 2002

(65) Prior Publication Data

US 2003/0119842 A1 Jun. 26, 2003

Related U.S. Application Data

(63) Continuation of application No. PCT/EP01/03772, filed on Apr. 3, 2001.

(30) Foreign Application Priority Data

Apr. 20, 2000 (DE) ................ 100 19 714

(51) Int. Cl.
*C07D 487/04* (2006.01)
*C07D 235/00* (2006.01)
*A61K 31/4188* (2006.01)

(52) U.S. Cl. ............... 514/249; 514/259.1; 514/292; 514/300; 544/281; 544/350; 546/84; 546/121

(58) Field of Classification Search .......... 544/281, 544/350; 546/84, 121; 514/249, 259.1, 514/292, 300
See application file for complete search history.

(56) References Cited

U.S. PATENT DOCUMENTS

| 3,792,166 A | 2/1974 | Spicer et al. ............. 424/270 |
| 3,894,022 A | 7/1975 | Hardtmann ............. 260/256.4 |
| 4,183,932 A | 1/1980 | Yamamoto et al. ......... 424/251 |
| 4,650,796 A | 3/1987 | George et al. ............. 514/213 |
| 5,068,244 A | 11/1991 | Moura et al. ............. 514/428 |
| 5,536,853 A | 7/1996 | Spellmeyer et al. ........ 549/441 |

FOREIGN PATENT DOCUMENTS

| DE | 100 19 714 A1 | 1/2002 |
| EP | 0 068 378 A1 | 1/1983 |
| EP | 0 353 047 B1 | 10/1994 |
| GB | 1135893 | 12/1968 |
| GB | 2 039 882 A | 8/1980 |

OTHER PUBLICATIONS

H. Bienayme et al., *Eine neue heterocyclische Mehrkomponentenreaktion füdie kombinatorische Synthese von anellierten 3-Aminoimidazolen*, Angew Chem. (1998) 110:2349-2352.

S. Chayer et al., *Regiospecific Thermal C-Acylation of Imidazo [1,2-a] Pyridines via an N-Acylimidazolium Intermediate*, Tetrahedron Letters 39 (1998) 9685-9688.

C. Blackburn, *A three-Component Solid-Phase Synthesis of 3-Aminoimidazol [1,2-a]azines*, Tetrahedron Letters 39 (1998) 5469-5472.

J. J. Kaminski, et al., *Antiulcer Agents. 2. Gastric Antisecretory, Cytoprotective, and Metabolic Properties of Substituted Imidazo[1,2-a]pyridines and Analogues*, J. Med. Chem. (1987) 30:2031-2046.

Y. Rival, et al., *Synthesis and Antibacterial Activity of Some Imidazo[1,2-a] pyrimidine Derivatives*, Chem. Pharm. Bull. (1992), 40(5):1170-1176.

M. Fisher, et al., *Imidazo[1,2-a]pyrimidine Anthelmintic and Antifungal Agents*, Journal of Medicinal Chemistry (1972), 15(9):982-985.

A. Gueiffier, et al., *Synthesis of Imidazo[1,2-a]pyridines as Antiviral Agents*, J. Med. Chem. (1998), 41:5108-5112.

G. Barlin, *Imidazo[1,2-b]pyridazines: Syntheses and Interaction with Central and Peripheral-Type (Mitochondrial) Benzodiazepine Receptors*, J. Heterocyclic Chem. (1998), 35:1205-1217.

K. Groebke, et al., *Synthesis of Imidazo[1,2-a] annulated Pyridines, Pyrazines and Pyrimidines by a Novel Three-Component Condensation*, SYNLETT, (Jun. 1998), 661-663.

C. Blackburn, et al., *Parallel Synthesis of 3-Aminoimidazo[1,2-a]pyridines and pyrazines by a New Three-Component Condensation*, Tetrahedron Letters 39 (1998) 2635-3638.

*Primary Examiner*—Deepak Rao
(74) *Attorney, Agent, or Firm*—Crowell & Moring LLP

(57) ABSTRACT

Salts of a bicyclic, N-acylated imidazo-3-amine or an imidazo-5-amine of the formula:

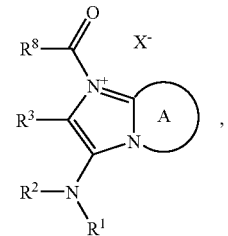

addition products thereof with acids, and methods for preparing the salts and addition products. Also disclosed are pharmaceutical compositions comprising the same and methods using the pharmaceutical compositions for the treatment or prophylaxis of pain, drug or alcohol abuse, diarrhoea, gastritis, ulcers, urinary incontinence, depression, narcolepsy, overweight, asthma, glaucoma, tinnitus, itching, hyperkinetic syndrome, epilepsy, or schizophrenia, for inducing anesthesia, and for anxiolysis.

32 Claims, 3 Drawing Sheets

SALTS OF BICYCLIC, N-ACYLATED IMIDAZO-3-AMINES AND IMIDAZO-5-AMINES

CROSS REFERENCE TO RELATED APPLICATIONS

The present application is a continuation of international patent application no. PCT/EP01/03772, filed Apr. 3, 2001, designating the United States of America, and published in German as WO 01/81344, the entire disclosure of which is incorporated herein by reference. Priority is claimed based on Federal Republic of Germany patent application no. 100 19 714.0, filed Apr. 20, 2000.

FIELD OF THE INVENTION

The present invention relates to salts of bicyclic, N-acylated imidazo-3-amines and imidazo-5-amines, to a process for producing them, to their use for producing pharmaceutical compositions and to pharmaceutical compositions containing these compounds.

BACKGROUND OF THE INVENTION

Individual compounds from the category of non-acylated bicyclic imidazo-3-amines and imidazo-5-amines which form the basis of the compounds according to the present invention are known to have interesting pharmacological properties. Thus, certain imidazo[1,2-a]pyridines are described as blood pressure-reducing active ingredients (GB-B-1,135,893), as anthelmintics and antimycotics (J. Med. Chem. 1972, 15, 982–985) and as anti-secretory active ingredients for the treatment of inflammatory diseases (EP-A-0 068 378). EP-A-0 266 890 and J. Med. Chem. 1987, 30, 2031–2046 also describe an effect of individual imidazopyridines against inflammatory diseases, in particular of the stomach. Further pharmacological effects described for individual representatives of the category of non-acylated imidazo-3-amines and imidazo-5-amines are antibacterial properties (Chem. Pharm. Bull. 1992, 40, 1170), antiviral properties (J. Med. Chem. 1998, 41 5108–5112) and the effect as benzodiazepine-receptor antagonist (J. Heterocyclic Chem. 1998, 35, 1205–1217).

Greater interest has been shown in the category of non-acylated bicyclic imidazo-3-amines and imidazo-5-amines in that multicomponent reactions which are suitable for automated combinational chemistry have been developed for the synthesis thereof. Whereas the isolated intermediate product continues reacting in the next step in conventional reaction sequences, equilibrium reactions take place between the educts and various intermediate products in multicomponent reactions, so a stable product is formed. The multicomponent reaction is particularly efficient if the desired product markedly predominates in the state of equilibrium, or is even removed from the equilibrium by irreversible reaction conditions. Ideally, it should also be possible to use as many variable and readily obtainable educts as possible in a multicomponent reaction which can be employed for combinational chemistry.

Thus, C. Blackburn et al., in Tetrahedron Lett. 1998, 39, 3635–3638, describe a three-component condensation for the parallel synthesis of bicyclic imidazo-3-amines and imidazo-5-amines. The synthesis publicized by K. Groebke et al., in Synlett 1998, 661–663 is similar to the synthesis in that reaction. H. Bienayme and K. Bouzid also describe a multicomponent reaction for the combinational synthesis of bicyclic imidazo-3-amines with which isolated imidazo-5-amines have also been produced in Angew. Chem. 1998, 110 (16), 2349–2352.

N-acylated bicyclic imidazo-3-amines were previously known only in so far as Chayer et al., in Tetrahedron Lett. 1998, 39, 9685–9688, describing salts of N-acylated imidazo[1,2-a]pyridines unsubstituted in the 3-position as intermediate stage in the production of the corresponding compounds C-acylated in the 3-position.

Furthermore, only N-acylation at the amino nitrogen is described for individual bicyclic imidazo-3-amines produced by solid phase synthesis (Blackburn in Tetrahedron Lett. 1998, 39, 5469–5472).

DESCRIPTION OF THE INVENTION

Figure 1:
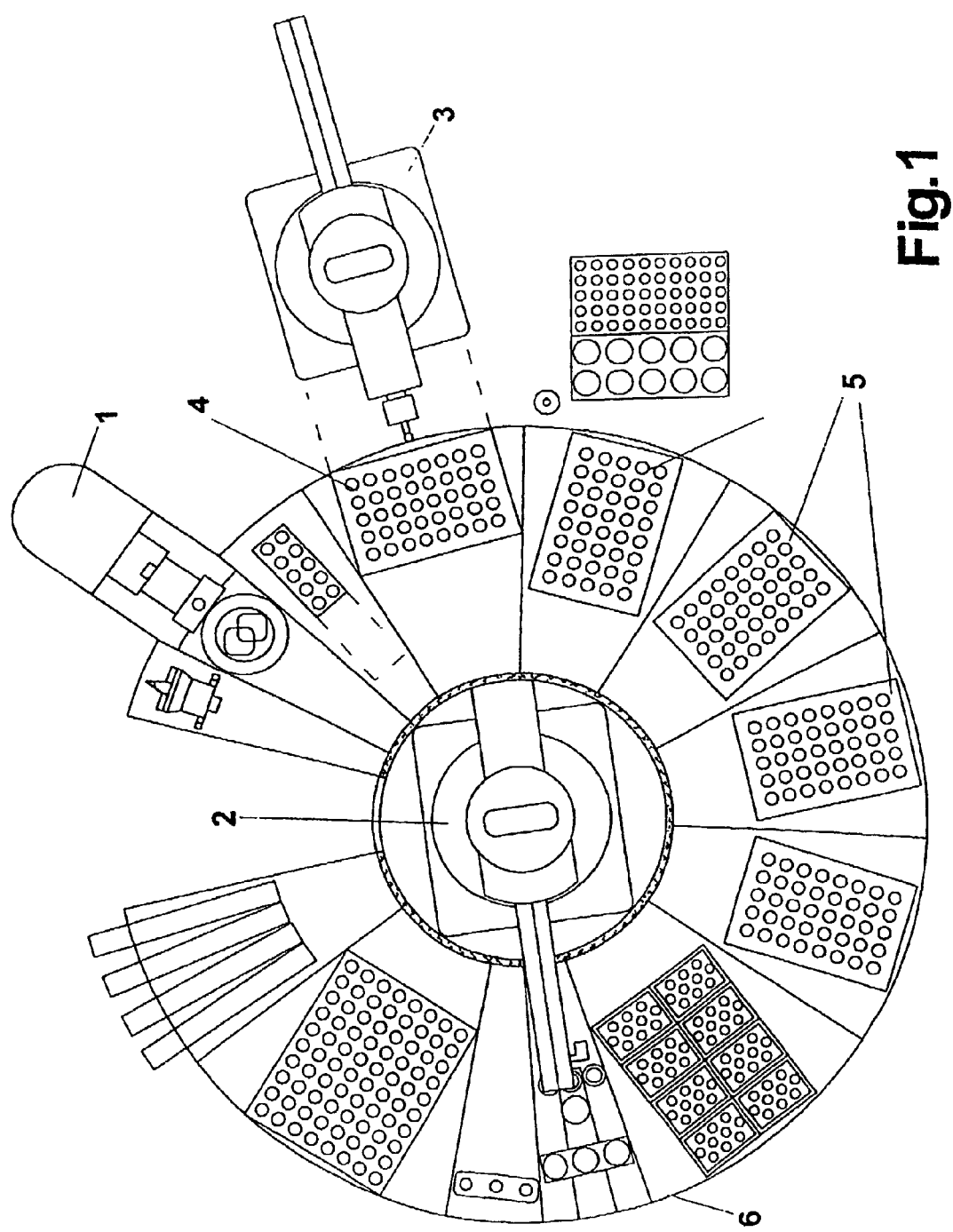
FIG. 1 shows a schematic representation of an automatic unit used for process step a) for the synthesis of the salt of the present invention.

It was accordingly an object of the present invention to prepare salts of bicyclic imidazo-3-amines and imidazo-5-amines N-acylated at the imidazole nitrogen, for the first time.

This object has been achieved according to the invention by preparing the salts of bicyclic, N-acylated imidazo-3-amines and imidazo-5-amines of general Formula I

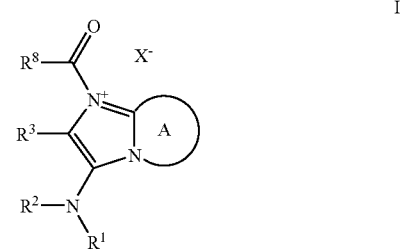

I wherein $R^1$ represents tert-butyl; 1,1,3,3-tetramethylbutyl; $(CH_2)_n$ CN where n=4, 5 or 6; optionally substituted phenyl; $C_4$–$C_8$ cycloalkyl, $CH_2CH_2R$ (R=4-morpholino); or $CH_2R^a$,
    wherein $R^a$ represents hydrogen; straight or branched $C_1$–$C_8$ alkyl; optionally substituted phenyl, CO(OR') (where R'=straight or branched $C_1$–$C_8$ alkyl); PO(OR")$_2$ (where R"=straight or branched $C_1$–$C_4$ alkyl); or Si($R^x R^y R^z$) (where $R^x$, $R^y$ and $R^z$ each independently represents straight or branched $C_1$–$C_4$ alkyl, $C_4$–$C_8$ cycloakyl or phenyl), $R^2$ represents hydrogen; $COR^b$, wherein $R^b$ represents straight or branched $C_1$–$C_8$ alkyl; straight or branched $C_1$–$C_8$ alkoxy; $C_3$–$C_8$ cycloalkyl; $CH_2CH_2CO(OR')$ (where R'=straight or branched $C_1$–$C_4$ alkyl); adamantyl; optionally substituted phenyl; benzyloxy; optionally substituted 1-naphthyl or 2-naphthyl or respectively optionally substituted 2-pyridyl, 3-pyridyl, 4-pyridyl, thiazolyl or furyl; CH$_2$R$^c$, wherein R$^c$ represents hydrogen, straight or branched C$_1$–C$_8$ alkyl or optionally substituted phenyl; CH$_2$CH$_2$R$^d$, wherein R$^d$ represents optionally substituted phenyl, or CONHR$^e$, wherein R$^e$ represents branched or straight C$_1$–C$_8$ alkyl; aryl; heteroaryl; C$_3$–C$_8$ cycloalkyl; or an aryl bound via a C$_1$–C$_3$ alkylene group, heteroaryl or C$_3$–C$_8$ cycloalkyl radical or in particular phenyl, R$^3$ represents straight or branched C$_1$–C$_8$ alkyl; C$_3$–C$_8$ cycloalkyl; optionally substituted phenyl; optionally substituted 1-naphthyl; 2-naphthyl; quinoline; anthracene; phenanthrene; benzothiophene; benzofurfuryl; optionally substituted pyrrole; 2-, 3- or 4-pyridyl; optionally substituted furfuryl; or optionally substituted thiophene, A represents a three-membered ring fragment selected from one of the following formulae:

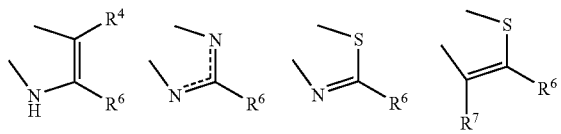

or a four-membered ring fragment selected from one of the following formulae:

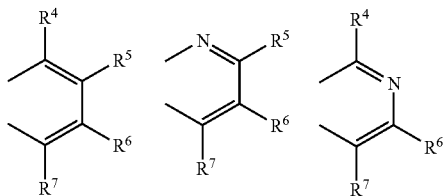

wherein R$^4$, R$^5$, R$^6$ and R$^7$ each independently represents hydrogen; straight or branched C$_1$–C$_8$ alkyl; fluorine; chlorine; bromine; CF$_3$; CN; NO$_2$; NHR$^f$, wherein R$^f$ represents hydrogen, straight or branched C$_1$–C$_8$ alkyl, or COR''' (R'''=straight or branched C$_1$–C$_4$ alkyl, or optionally substituted phenyl); SR$^g$, wherein R$^g$ represents hydrogen, straight or branched C$_1$–C$_4$ alkyl, optionally substituted phenyl, optionally substituted pyridine, optionally substituted benzyl, or optionally substituted fluorenyl; OR$^h$, wherein R$^h$ represents hydrogen, straight or branched C$_1$–C$_8$ alkyl, COR''' (R'''=straight or branched C$_1$–C$_4$, alkyl or optionally substituted phenyl), or CO(OR$^i$) (R$^i$=straight or branched C$_1$–C$_8$ alkyl); CO(OR$^i$) or CH$_2$CO(OR$^i$), wherein R$^i$ respectively represents branched or straight C$_1$–C$_8$ alkyl or optionally substituted phenyl;

or R$^6$ and R$^7$ together represent a ring fragment —CR$^i$=CR$^j$—CH=CH—, wherein R$^i$ and R$^j$ each represents hydrogen, or one of the two radicals R$^i$ or R$^j$ differs from hydrogen and represents F, Cl, Br, I or straight or branched C$_1$–C$_8$ alkyl, whereas R$^4$ and R$^5$ independently thereof have the meaning given above, R$^8$ represents branched or straight C$_1$–C$_8$ alkyl; aryl; heteroaryl; C$_3$–C$_8$ cycloalkyl; or an aryl bound by a C$_1$–C$_3$ alkylene group, heteroaryl, or C$_3$–C$_8$ cycloalkyl radical, and X represents the anion of an inorganic or organic acid.

The broken lines in the formula

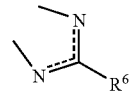

mean that there is a double bond between one of the nitrogen atoms and the C-atom bound to R$^6$ whereas the free binding site is saturated by a hydrogen atom in the other nitrogen atom.

Preferred according to the invention are salts of bicyclic, N-acylated imidazo-3-amines and imidazo-5-amines of Formula I, in which R$^2$ represents hydrogen, R$^1$ is selected from the group consisting of (CH$_2$)$_6$CN, cyclohexyl, CH$_2$CO(Omethyl), 2,6-dimethylphenyl, tert-butyl and CH$_2$CH$_2$R(R=4-morpholino), and R$^3$ is selected from the group consisting of 4-acetamidophenyl, 2-bromophenyl, 3-bromophenyl, 4-bromophenyl, 4-bromo-2-fluorophenyl, 5-bromo-2-fluorophenyl, 3-bromo-4-fluorophenyl, 4-tert. butylphenyl, 2-chloro-4-fluorophenyl, 2-chloro-6-fluorophenyl, 2-chlorophenyl, 3-chlorophenyl, 4-chlorophenyl, 4-cyanophenyl, 2,3-dichlorophenyl, 2,4-dichlorophenyl, 3,4-dichlorophenyl, 2,3-dimethoxyphenyl, 3,4-dimethoxyphenyl, 2,4-dimethylphenyl, 2,5-dimethylphenyl, 2-fluorophenyl, 3-fluorophenyl, 4-fluorophenyl, 4-hexylphenyl, 3-hydroxyphenyl, 2-methoxyphenyl, 2-methylphenyl, 3-methylphenyl, 4-methylphenyl, 4-nitrophenyl, 3-phenoxyphenyl, 4-(1-pyrrolidino)-phenyl, 2-(trifluoromethyl)phenyl, 3-(trifluoromethyl)phenyl, 4-(trifluoromethyl)-phenyl, 3,4,5-trimethoxyphenyl, 3-(4-chlorophenoxy)phenyl, 4-acetoxy-3-methoxyphenyl, 4-dimethylaminonaphthyl, 2-ethoxynaphthyl, 4-methoxynaphthyl, 2-(1-(phenylsulfonyl)-pyrrole), 2-(N-methylpyrrole), 2-(N-(3,5-dichlorophenyl)pyrrole), 2-(1-(4-chlorophenyl)pyrrole), 2-(5-acetoxymethylfurfuryl), 2-(5-methylfurfuryl), 2-(5-nitrofurfuryl), 2-[5-(3-nitrophenyl)furfuryl], 2-[5-(2-nitrophenyl)furfuryl], 2-(5-bromofurfuryl), 2-[5-(4-chlorophenyl)furfuryl], 2-(4,5-dimethylfurfuryl), 2-[5-(2-chlorophenyl)furfuryl], 2-(5-ethylfurfuryl), 2-[5-(1,3-dioxalanfurfuryl], 2-(5-chlorothiophenyl), 2-(5-methylthiophenyl), 2-(5-ethylthiophenyl), 2-(3-methylthiophenyl), 2-(4-bromothiophenyl), 2-(5-nitrothiophenyl), 5-(2-carboxylic acid thiophenyl), 2-[4-(phenylethyl)-thiophenyl], 2-[5-(methylthio)thiophenyl], 2-(3-bromothiophenyl), 2-(3-phenoxythiophenyl), and 2-(5-bromothiophenyl). R$^3$ is particularly preferred to be methyl, cyclohexyl, phenyl, furan-2-yl, 2-pyridyl or 2-thiophenyl.

Further preferred salts are those of bicyclic N-acylated imidazo-3-amines and imidazo-5-amines in which A represents a three-membered ring fragment of formula

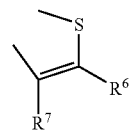

or a four-membered ring fragment selected from one of the formulae

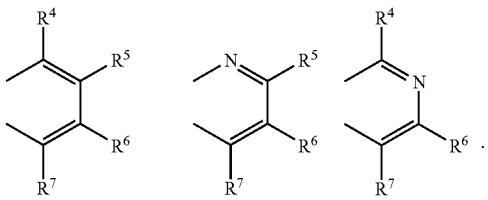

In the salts of bicyclic, N-acylated imidazo-3-amines and imidazo-5-amines of Formula I according to the invention, moreover, the radicals $R^4$, $R^5$, $R^6$ and $R^7$ are preferably selected independently from one another from the group consisting of hydrogen; methyl; ethyl; isopropyl; n-propyl; n-butyl; fluorine; bromine; $CF_3$; CN; $NO_2$; $NHR^f$, wherein $R_f$ represents hydrogen, methyl, ethyl, n-propyl, n-butyl, C(O)methyl, or C(O)phenyl; $SR^g$, wherein $R^g$ represents hydrogen, methyl, ethyl, n-propyl, n-butyl, or phenyl; $OR^h$, wherein $R^h$ represents hydrogen, methyl, ethyl, n-propyl, n-butyl, phenyl, COmethyl, COphenyl CO(Omethyl), or CO(Oethyl); and $CO(OR^i)$ or $CH_2CO(OR^i)$, wherein $R^i$ respectively represents methyl, ethyl, n-propyl, n-butyl, or phenyl. Hydrogen, methyl, chlorine, $NH_2$ and $NO_2$ are particularly preferred.

In the salts of bicyclic, N-acylated imidazo-3-amines and imidazo-5-amines of Formula I according to the invention, $R^8$ preferably represents methyl; ethyl; n-propyl; n-butyl; n-pentyl; n-hexyl; or phenyl, cycolhexyl or 2-naphthyl unsubstituted, monosubstituted in the 4-position or disubstituted in the 2- and 6-position. Methyl, n-hexyl, 2,6-dichlorophenyl, 4-methoxyphenyl, cyclohexyl or 2-naphthyl are particularly preferred.

According to the present invention, the anion X of an inorganic or organic acid is preferably the anion of hydrobromic acid, sulphuric acid, methane sulphonic acid, formic acid, acetic acid, oxalic acid, succinic acid, tartaric acid, mandelic acid, fumaric acid, lactic acid, citric acid, glutamic acid or aspartic acid or, in particular, hydrochloric acid.

As the salts of Formula I still have at least one basic nitrogen atom, they may be converted into addition products in a known manner by acids, preferably physiologically acceptable acids, for example hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid and/or aspartic acid. Trimethyl chlorosilane in aqueous solution is also suitable for producing the HCl addition product. The present invention also relates to these addition products.

Particularly preferred salts according to the invention are those of bicyclic, N-acylated imidazo-3-amines and imidazo-5-amines and their addition products selected from the group consisting of:
1-acetyl-3-tert-butylamino-2-phenyl-imidazo[1,2-a]-pyridin-1-ium chloride,
1-acetyl-3-tert-butylamino-2-phenyl-imidazo[1,2-a]-pyrazin-1-ium chloride,
1-acetyl-3-tert-butylamino-2-phenyl-imidazo[1,2-a]-pyrimidin-1-ium chloride,
7-acetyl-5-tert-butylamino-6-phenyl-imidazo[2,1-b]-thiazol-7-ium chloride,
3-acetyl-1-cyclohexylamino-2-phenyl-imidazo[1,2-a]-quinolin-3-ium chloride,
1-acetyl-3-cyclohexylamino-2-phenyl-imidazo[1,2-a]-pyrimidin-1-ium chloride,
1-acetyl-8-benzyloxy-3-cyclohexylamino-2-methyl-imidazo[1,2-a]pyridin-1-ium chloride,
1-acetyl-8-benzyloxy-3-tert-butylamino-2-methyl-imidazo[1,2-a]pyridin-1-ium chloride,
1-acetyl-8-benzyloxy-2-methyl-3-(1,1,3,3-tetramethylbutylamino)imidazo[1,2-a]pyridin-1-ium chloride,
3-(tert-butyl-cyclohexancarbonyl-amino)-1-cyclohexancarbonyl-2-phenyl-imidazo[1,2-a]pyridin-1-ium chloride,
3-(tert-butyl-heptanoyl-amino)-1-heptanoyl-2-phenyl-imidazo[1,2-a]pyridin-1-ium chloride,
1-acetyl-3-cyclohexylamino-2-furan-2-yl-imidazo[1,2-a]pyridin-1-ium chloride,
1-acetyl-3-cyclohexylamino-2-furan-2-yl-imidazo[1,2-a]pyrimidin-1-ium chloride,
1-acetyl-5-amino-7-chloro-3-cyclohexylamino-2-furan-2-yl-imidazo[1,2-a]pyrimidin-1-ium chloride,
1-acetyl-3-cyclohexylamino-2-pyridin-2-yl-imidazo[1,2-a]pyridin-1-ium chloride,
1-acetyl-3-cyclohexylamino-6-nitro-2-pyridin-2-yl-imidazo[1,2-a]pyridin-1-ium chloride,
1-acetyl-3-cyclohexylamino-5-methyl-2-pyridin-2-yl-imidazo[1,2-a]pyridin-1-ium chloride,
1-acetyl-3-cyclohexylamino-2-pyridin-2-yl-imidazo[1,2-a]pyrazin-1-ium chloride,
1-acetyl-3-cyclohexylamino-2-pyridin-2-yl-imidazo[1,2-a]pyrimidin-1-ium chloride,
1-acetyl-5-amino-7-chloro-3-cyclohexylamino-2-pyridin-2-yl-imidazo[1,2-a]pyrimidin-1-ium chloride,
1-acetyl-3-cyclohexylamino-5,7-dimethyl-2-pyridin-2-yl-imidazo[1,2-a]pyrimidin-1-ium chloride,
7-acetyl-5-cyclohexylamino-6-pyridin-2-yl-imidazo[2,1-b]thiazol-7-ium chloride,
1-acetyl-2-cyclohexyl-3-cyclohexylamino-imidazo[1,2-a]pyridin-1-ium chloride,
1-acetyl-3-cyclohexylamino-2-methyl-imidazo[1,2-a]pyrimidin-1-ium chloride,
1-acetyl-5-amino-7-chloro-3-cyclohexylamino-2-methyl-imidazo[1,2-a]pyrimidin-1-ium chloride,
1-acetyl-5-amino-7-chloro-3-cyclohexylamino-2-thiophene-2-yl-imidazo[1,2-a]pyrimidin-1-ium chloride,
1-acetyl-5-amino-7-chloro-2-furan-2-yl-3-(methoxycarbonylmethylamino)imidazo[1,2-a]pyrimidin-1-ium chloride,
1-acetyl-2-cyclohexyl-3-(methoxycarbonylmethylamino)imidazo[1,2-a]pyridin-1-ium chloride,
1-acetyl-2-cyclohexyl-3-(methoxycarbonylmethylamino)imidazo[1,2-a]pyrimidin-1-ium chloride,
1-acetyl-3-(2,6-dimethyl-phenylamino)-2-methyl-6-nitro-imidazo[1,2-a]pyridin-1-ium chloride,
1-acetyl-5-amino-7-chloro-3-(2,6-dimethyl-phenylamino)-2-thiophene-2-yl-imidazo[1,2-a]pyrimidin-1-ium chloride, and
1-acetyl-3-cyclohexylamino-2-furan-2-yl-imidazo[1,2-a]pyridin-1-ium chloride hydrochloride.

In so far as the salts according to the invention of bicyclic, N-acylated imidazo-3-amines and imidazo-5-amines contain optically active carbon atoms, the present invention also relates to the enantiomers of these compounds and mixtures thereof.

The term aryl radical preferably denotes an optionally singly or multiply substituted phenyl or naphthyl radical.

The term heteroaryl radical denotes aromatic radicals comprising at least one heteroatom, preferably nitrogen, oxygen and/or sulphur, particularly preferably nitrogen and/or oxygen.

It has surprisingly also be found that the salts according to the invention of bicyclic, N-acylated imidazo-3-amines and imidazo-5-amines bind to the μ-opiate receptor and are therefore also suitable as pharmaceutical active ingredients.

The invention therefore also relates to pharmaceutical compositions containing, as active ingredient, at least one salt of a bicyclic, N-acylated imidazo-3-amine or imidazo-5-amine of general Formula I, in which $R^1$ to $R^8$ and A have the meaning given above and X represents the anion of a pharmaceutically acceptable inorganic or organic acid, preferably of hydrobromic acid, sulphuric acid, methane sulphonic acid, formic acid, acetic acid, oxalic acid, succinic acid, tartaric acid, mandelic acid, fumaric acid, lactic acid, citric acid, glutamic acid and/or aspartic acid, or in particular, hydrochloric acid. The active ingredient may also be additional products of a bicyclic, N-acylated imidazo-3-amine or imidazo-5-amine of general Formula I with a physiologically acceptable acid, preferably hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid and/or aspartic acid.

The pharmaceutical composition according to the invention preferably contains, as active ingredient, at least one salt of a bicyclic, N-acylated imidazo-3-amine or imidazo-5-amine or its acid addition product selected from the group consisting of:

1-acetyl-3-tert-butylamino-2-phenyl-imidazo[1,2-a]-pyridin-1-ium chloride,
1-acetyl-3-tert-butylamino-2-phenyl-imidazo[1,2-a]-pyrazin-1-ium chloride,
1-acetyl-3-tert-butylamino-2-phenyl-imidazo[1,2-a]-pyrimidin-1-ium chloride,
7-acetyl-5-tert-butylamino-6-phenyl-imidazo[2,1-b]-thiazol-7-ium chloride,
3-acetyl-1-cyclohexylamino-2-phenyl-imidazo[1,2-a]-quinolin-3-ium chloride,
1-acetyl-3-cyclohexylamino-2-phenyl-imidazo[1,2-a]-pyrimidin-1-ium chloride,
1-acetyl-8-benzyloxy-3-cyclohexylamino-2-methyl-imidazo[1,2-a]pyridin-1-ium chloride,
1-acetyl-8-benzyloxy-3-tert-butylamino-2-methyl-imidazo[1,2-a]pyridin-1-ium chloride,
1-acetyl-8-benzyloxy-2-methyl-3-(1,1,3,3-tetramethylbutylamino)imidazo[1,2-a]pyridin-1-ium chloride,
3-(tert-butyl-cyclohexancarbonyl-amino)-1-cyclohexancarbonyl-2-phenyl-imidazo[1,2-a]pyridin-1-ium chloride,
3-(tert-butyl-heptanoyl-amino)-1-heptanoyl-2-phenyl-imidazo[1,2-a]pyridin-1-ium chloride,
1-acetyl-3-cyclohexylamino-2-furan-2-yl-imidazo[1,2-a]pyridin-1-ium chloride,
1-acetyl-3-cyclohexylamino-2-furan-2-yl-imidazo[1,2-a]pyrimidin-1-ium chloride,
1-acetyl-5-amino-7-chloro-3-cyclohexylamino-2-furan-2-yl-imidazo[1,2-a]pyrimidin-1-ium chloride,
1-acetyl-3-cyclohexylamino-2-pyridin-2-yl-imidazo[1,2-a]pyridin-1-ium chloride,
1-acetyl-3-cyclohexylamino-6-nitro-2-pyridin-2-yl-imidazo[1,2-a]pyridin-1-ium chloride,
1-acetyl-3-cyclohexylamino-5-methyl-2-pyridin-2-yl-imidazo[1,2-a]pyridin-1-ium chloride,
1-acetyl-3-cyclohexylamino-2-pyridin-2-yl-imidazo[1,2-a]pyrazin-1-ium chloride,
1-acetyl-3-cyclohexylamino-2-pyridin-2-yl-imidazo[1,2-a]pyrimidin-1-ium chloride,
1-acetyl-5-amino-7-chloro-3-cyclohexylamino-2-pyridin-2-yl-imidazo[1,2-a]pyrimidin-1-ium chloride,
1-acetyl-3-cyclohexylamino-5,7-dimethyl-2-pyridin-2-yl-imidazo[1,2-a]pyrimidin-1-ium chloride,
7-acetyl-5-cyclohexylamino-6-pyridin-2-yl-imidazo[2,1-b]thiazol-7-ium chloride,
1-acetyl-2-cyclohexyl-3-cyclohexylamino-imidazo[1,2-a]pyridin-1-ium chloride,
1-acetyl-3-cyclohexylamino-2-methyl-imidazo[1,2-a]pyrimidin-1-ium chloride,
1-acetyl-5-amino-7-chloro-3-cyclohexylamino-2-methyl-imidazo[1,2-a]pyrimidin-1-ium chloride,
1-acetyl-5-amino-7-chloro-3-cyclohexylamino-2-thiophene-2-yl-imidazo[1,2-a]pyrimidin-1-ium chloride,
1-acetyl-5-amino-7-chloro-2-furan-2-yl-3-(methoxycarbonylmethylamino)imidazo[1,2-a]pyrimidin-1-ium chloride,
1-acetyl-2-cyclohexyl-3-(methoxycarbonylmethylamino)imidazo[1,2-a]pyridin-1-ium chloride,
1-acetyl-2-cyclohexyl-3-(methoxycarbonylmethylamino)imidazo[1,2-a]pyrimidin-1-ium chloride,
1-acetyl-3-(2,6-dimethyl-phenylamino)-2-methyl-6-nitro-imidazo[1,2-a]pyridin-1-ium chloride,
1-acetyl-5-amino-7-chloro-3-(2,6-dimethyl-phenylamino)-2-thiophene-2-yl-imidazo[1,2-a]pyrimidin-1-ium chloride, and
1-acetyl-3-cyclohexylamino-2-furan-2-yl-imidazo[1,2-a]pyridin-1-ium chloride hydrochloride.

The salts according to the invention have, in particular, analgesic activity. Therefore, a particularly preferred embodiment of the invention is the use of salts of at least one bicyclic N-acylated imidazo-3-amine or imidazo-5-amine of general Formula I, in which $R^1$ to $R^8$ A and X have the meaning given above and/or of their addition products with a physiologically acceptable acid for producing a pharmaceutical composition for the treatment of pain, and methods of treating pain using the composition.

These active ingredients are also suitable, in particular, for the treatment of drug and/or alcohol abuse, diarrhoea, gastritis, ulcers, urinary incontinence, depression, narcolepsy, excess weight, asthma, glaucoma, tinnitus, itching and/or hyperkinetic syndrome. They are also suitable for the treatment/prophylaxis of epilepsy and schizophrenia, and/or for anxiolysis and/or anaesthesia.

The pharmaceutical compositions according to the invention, in particular as pain-killers (analgesics) contain excipients, fillers, solvents, diluents, colorants and/or binders in addition to at least one salt of Formula I or its addition product with a physiologically acceptable acid. The choice of auxiliary materials and the amounts to be used are determined in a manner known to a person skilled in the art and depend on whether the pharmaceutical composition is to be administered orally, intravenously, intraperitoneally, intradermally, intramuscularly, intranasally, buccally or topically, for example to infections of the skin, the mucous membranes and the eyes. Preparations in the form of tablets, dragees, capsules, granules, droplets, juices and syrups are suitable for oral administration, solutions, suspensions, readily reconstitutable dry preparations as well as sprays for parenteral, topical and inhalative administration. Salts of Formula I according to the present invention or their addition products with physiologically acceptable acids deposited in dissolved form or in a plaster, optionally with addition of agents which promote skin penetration are preparations which are suitable for percutaneous administration. Suitably formulated oral or percutaneous preparations are able to release in a controlled or delayed manner the salts of Formula I according to the present invention or their addition products with physiologically acceptable acids.

The amount of active ingredient to be administered to the patient varies according to the patient's weight, the method of administration, the indication and the severity of the disease. It is normal to administer 2 to 500 mg/kg of the salts of bicyclic, N-acylated imidazo-3-amines or imidazo-5-amines of Formula I or their addition products with physiologically acceptable acids.

The present invention also relates to processes for producing the salts of bicyclic, N-acylated imidazo-3-amines and imidazo-5-amines of Formula I and their addition products with acids. These processes comprise the following process steps:

a) producing the imidazo-3-amines and imidazo-5-amines by three-component reaction from amidine, aldehyde and isonitrile in a solvent, preferably dichloromethane, and in the presence of an acid, preferably perchloric acid, wherein the starting compounds are added in succession in the sequence of amidine, aldehyde and isonitrile, b) optionally for producing compounds in which $R^2$ is not hydrogen, reacting the products formed in step a) with a compound $R^2$Hal (Hal=bromine, iodine or in particular chlorine) or an isocyanate, c) converting the reaction product from step a) or b) with preferably at least a quadruple molar excess of an acid chloride $R^8C(O)Cl$, d) removing the excess acid chloride from the reaction mixture on completion of the reaction, e) optionally exchanging the chloride in a manner well-known to those ordinarily skilled in the art for a different acid radical, preferably of hydrobromic acid, sulphuric acid, methane sulphonic acid, formic acid, acetic acid, oxalic acid, succinic acid, tartaric acid, mandelic acid, fumaric acid, lactic acid, citric acid, glutamic acid or aspartic acid, f) optionally producing the addition product according to the invention with a preferably physiologically acceptable acid.

Process step a) is preferably carried out by reacting amidines of general Formula II, in particular 3-aminopyrazole, 3-amino-1,2,4-triazole, 2-amino-1,3,4-thiadiazole, 2-aminothiazole, 2-aminopyridine, 2-aminopyrimidine and 2-aminopyrazine derivatives, which are available commercially from companies such as Acros, Avocado, Aldrich, Fluka, Lancaster, Maybridge, Merck, Sigma or TCI-Jp, with a wide variety of aldehydes of Formula III and isonitriles of Formula IV in the presence of 20% perchloric acid by a three-component reaction to form compounds of Formula V. R1 and R3 as well as A have the meaning given above for compounds of Formula I.

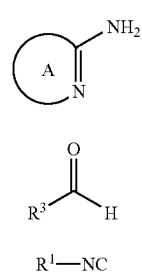

II

III

IV

-continued

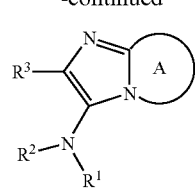

V

Reaction step a) is carried out in a solvent, preferably dichloromethane (DCM), at a temperature of −20° C. to 100° C., preferably at 0° C. to 40° C. and particularly preferably at 10° C. to 20° C.

For producing the compounds according to the invention in which $R^2$ does not represent hydrogen, the compounds V formed in reaction step a) were dissolved in a solvent, preferably tetrahydroform (THF) or DCM, and, depending on the desired end product, were reacted with a compound $R^2$Hal, wherein Hal represents bromine, iodine or, in particular, chlorine, for example an optionally substituted alkyl, aryl or acid chloride or, if $R^2$ represents $CONHR^8$, as mentioned above, with an isocyanate in the presence of an inorganic or organic base, preferably in the presence of a morpholine resin (for example polystyrene morpholine manufactured by Argonaut), in a solvent, preferably dichloromethane, within 2 to 24 hours at temperatures between −20° C. and 100° C., preferably between 10° C. and 40° C., to form compounds of Formula VI, in which $R^2$ does not represent hydrogen:

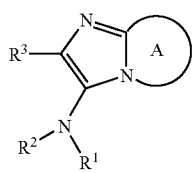

VI

Then, in reaction step c), the reaction product V from reaction step a) or the reaction product VI from reaction step b), in which $R^2$ does not represent hydrogen, is reacted with an excess, preferably an excess of at least four-fold, in particular a four- to tenfold excess of an acid chloride $R^8C(O)Cl$ to form the below-mentioned salt of Formula Ia according to the invention, wherein $R^8$ has the meaning given above for Formula I. This reaction step is carried out in a solvent, preferably in an ether or halogenated hydrocarbon, particularly preferably in THF or DCM, at a temperature between −20° C. and 100° C., preferably between 0° C. and 60° C.

If a reaction product V from reaction step a) is reacted in this way, a product of Formula I according to the invention, in which $R^2$ is not a hydrogen atom but an acid radical $COR^b$, $R^b$ being identical to $R^8$, can also be obtained in this step. This product may be a by-product or the main product or sole product of the reaction, depending on the reaction conditions. For the specific production of this product, it is preferable to employ a very large excess, in particular at least a tenfold excess of the acid chloride and/or at high temperature and/or for a long reaction period. Any product mixtures obtained may be separated from a solvent or solvent mixture by known processes, for example by chromatography or preferably in process step f) by precipitation of the addition product with an acid.

Preferably 2 to 12 hours after addition of the acid chloride in process steps c), the excess acid chloride is removed from the reaction mixture in process step d). This can basically be effected by conventional methods known to a person ordinarily skilled in the art, for example under vacuum or by using inorganic or organic bases. According to the invention, however, it is preferable to carry out this separation in a heterogeneous phase, in particular by addition of a scavenger resin. (Tris-(2-aminoethyl)amine-polystyrene is preferably used as scavenger resin. The following reaction diagram gives examples of the particularly preferred embodiment of process steps c) and d):

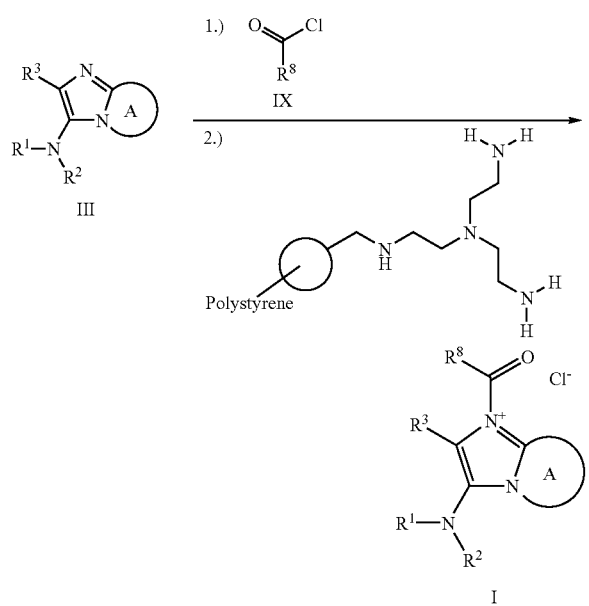

For producing the salts of Formula I according to the invention, in which X represents an acid radical different from chloride, the chloride is optionally exchanged in a manner well-known to a person ordinarily skilled in the art in process step e) for the radical of a different organic or inorganic acid, preferably hydrobromic acid, sulphuric acid, methane sulphonic acid, formic acid, acetic acid, oxalic acid, succinic acid, tartaric acid, mandelic acid, fumaric acid, lactic acid, citric acid, glutamic acid or aspartic acid. Suitably prepared basic ion exchangers are preferably used here.

The process according to the invention can also be carried out, in particular, in automatic synthesis units.

Protective group strategies may also be employed for the specific production of compounds of Formula I according to the invention from reaction products V of reaction step a) in which $R^2$ represents a hydrogen atom (P. J. Kocienski, Protecting Groups, Thieme Verlag, 1994; T. W. Greene, P. G. M. Wuts, Protective Groups in Organic Synthesis, John Wiley & Sons, 3rd edition, 1999). For this purpose, the $R^2N$ grouping is preferably converted into a carbamate, particularly preferably into a benzyl or tert.-butylcarbamate, or an amide or $R^2$ into a silyl group, preferably tert.-butyldimethylsilyl or trimethylsilyl. These protective groups may optionally be removed after the reaction with an acid chloride $R^8C(O)Cl$ in a manner well-known to those of ordinary skill in the art.

Process step f) is preferably carried out by reacting the reaction product from step d) or e) with physiologically acceptable acids, preferably hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid and/or aspartic acid, in a solvent or solvent mixture, preferably diethyl ether, diisopropyl ether, alkyl acetate, acetone and/or 2-butanone, wherein the resultant addition product precipitates, optionally after removal of a proportion of the solvent or addition of a further non-polar solvent, for example a hydrocarbon or aliphatic ether. The reaction with an aqueous solution of trimethylchlorosilane is particularly preferred for producing the HCl addition product. According to the invention, process step f) is preferably also used for cleaning the salts according to general Formula I. In this case, the salt is liberated from the addition product in the conventional manner after the above-described precipitation.

If a salt of Formula I is produced using process step d) and process step f) and is used for cleaning purposes, process step f) can alternatively or additionally be carried out prior to process step d).

EXAMPLES

The following examples serve to illustrate the invention without restricting it.

Figure 2:
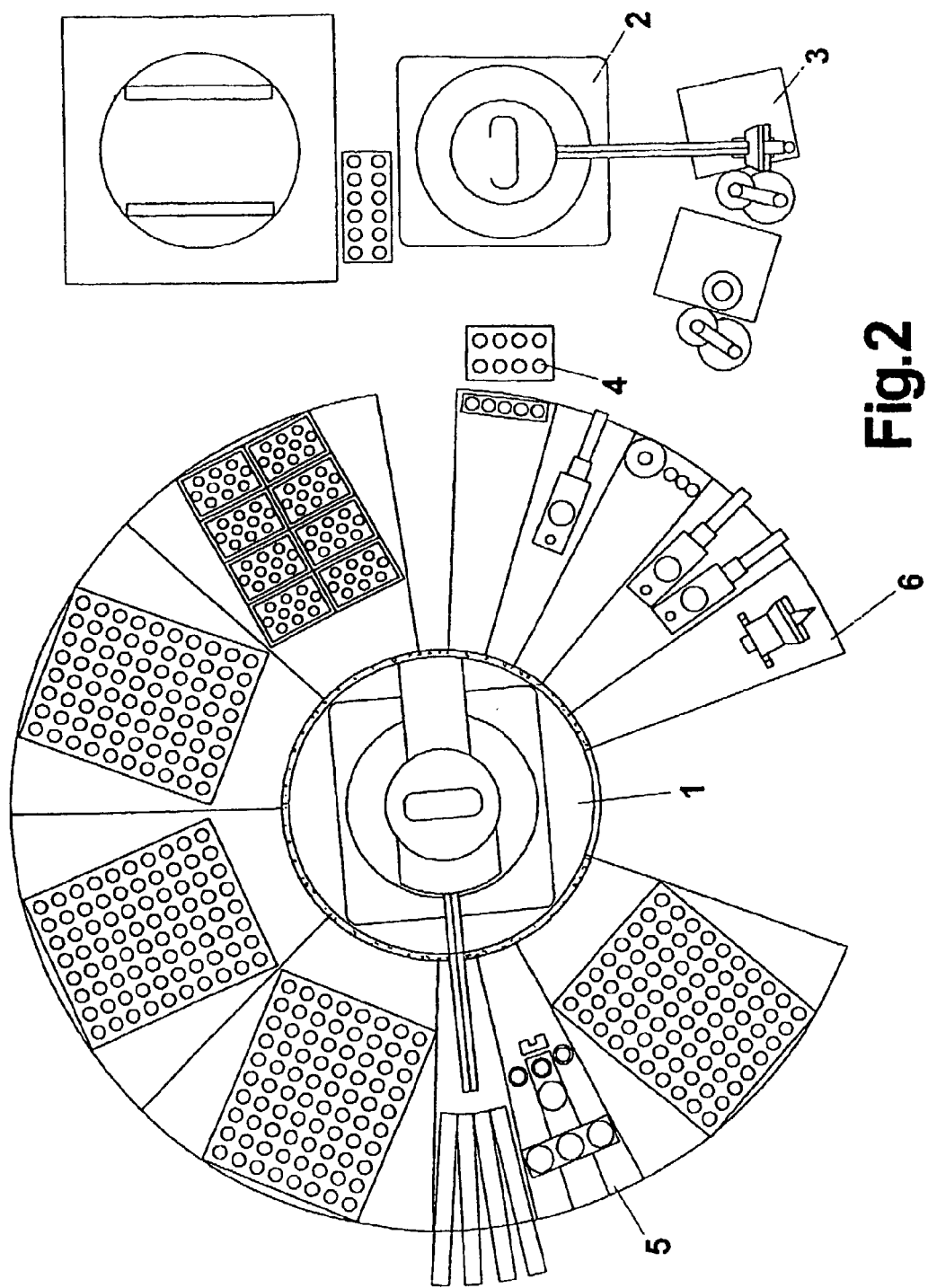
FIG. 2 shows a schematic representation of another automatic unit used for process step a) for the synthesis of the salt of the present invention.

General Directions for Synthesis of the Imidazoles of Formula V (Process Step a)):

The imidazoles of Formula V were synthesized on an automatic unit manufactured by Zymark, as shown in FIG. 1 and FIG. 2.

FIG. 1 comprises a Capper station (Ref. 1) for closing the reaction tube, a robot 1 (Ref. 2) and a robot 2 (Ref. 3), wherein robot 1 moves the reaction tubes and the corresponding racks and robot 2 pipettes the reagents into the reaction tubes, a reactor block with controllable temperature (Ref. 4), stirrer blocks (Ref. 5) and a filtration station (Ref. 6), in which the reaction solution is filtered off.

FIG. 2 also comprises a robot 1 (Ref 1) and a robot 2 (Ref. 2) which both move the glass tubes with the synthetic products onto the various stations. The stations are, in particular, a vortexer (Ref 3) for thoroughly mixing the samples and for adding solutions or solvents, a spin reactor (Ref 4) for thoroughly mixing samples, a phase detection station (Ref 5) for detecting the phase boundary and phase separation and a station (Ref. 6) for drying the synthetic products over salt cartridges.

Synthesis was carried out in accordance with the following general directions:

A round-bottomed glass tube (diameter 16 mm, length 125 mm) with screw thread was equipped manually with a stirrer and closed with a screw cap with septum on the Capper station. The tube was placed by robot 1 in the reactor block adjusted to 15° C. Robot 2 added the following reagents in succession by pipetting:

1) 1 ml of a 0.1 M amidine solution+20% $HClO_4$ in dichloromethane 2) 0.5 ml of a 0.3 M aldehyde solution in dichloromethane 3) 0.575 ml of a 0.2 M isonitrile solution in dichloromethane.

The reaction mixture was stirred for 660 min at 15° C. in one of the stirrer blocks. The reaction solution was then filtered off at the filtration station. The tube was washed twice with 1 ml dichloromethane and 200 µl water in each case.

The rack with the tubes was then placed manually on the processing unit (FIG. 2). 3 ml of a 10% NaCl solution and 1.5 ml dichloromethane were added to the reaction mixture on a vortexer there. The components were mixed thoroughly for ten minutes in the spin reactor and a clear phase boundary was formed by slowly reducing the rotating movement. This phase boundary was detected optically and the organic phase removed by a pipette. A further 1.5 ml of dichloromethane was added to the reaction mixture in the next step. The solution was shaken and centrifuged and the organic phase removed by pipette. The combined organic phases were dried over 2.4 g $MgSO_4$ (granulated). The solvent was removed in a vacuum centrifuge.

Figure 3:
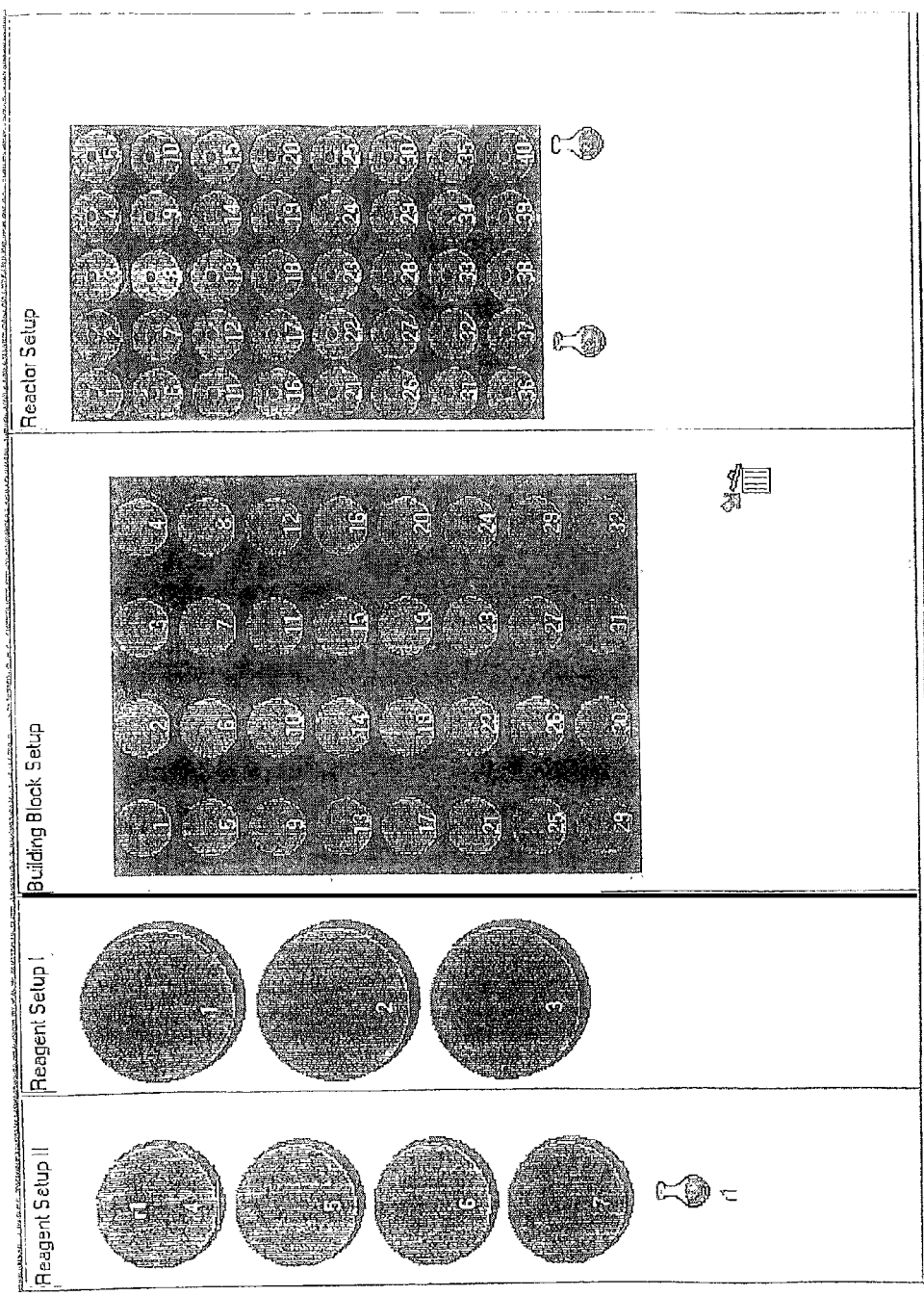
FIG. 3 shows a schematic representation of an automatic unit used for process steps c) and d) for the synthesis of the salt of the present invention.

General Directions for Process Steps c) and d):

The following examples of the salts of Formula I according to the invention (process steps c) and d)) were synthesized on a synthetic robot manufactured by MultiSyntech (FIG. 3). The synthetic robot comprises a heatable and coolable reaction block with 40 stirring positions, a reagent rack with 32 positions, seven larger vessels for reagents and two pipetting arms for addition of solvents and reagents. The salts of Formula I according to the invention were produced by the following general directions:

0.1 mmol of imidazole was pipetted in a glass tube which had previously been placed manually in the reactor block. After adding 2 ml THF and stirring for about 10 min, 0.4 mmol of the acid chloride is added. The reaction mixture is stirred for 6 h at ambient temperature. 0.5 mmol of the scavenger resin (Tris-(2-aminoethyl)amine-polystyrene 2.43 mmol/g was added manually in the following step. After stirring for 2 h, the reaction solution was separated from the resin by filtration, washed three times with 1.5 ml dichloromethane in each case and concentrated in a vacuum centrifuge.

If production is not described here, the chemicals and solvents used have been obtained commercially from the normal suppliers (Acros, Avocado, Aldrich, Fluka, Lancaster, Maybridge, Merck, Sigma, TCI-Jp, Novabiochem). All products were analyzed by NMR or ESI-MS.

Example 1

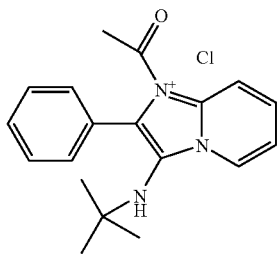

1-acetyl-3-tert-butylamino-2-phenyl-imidazo[1,2-a]-pyridin-1-ium chloride

Example 1 was carried out in accordance with the general directions for synthesis in process step a) from 1.0 ml (0.1 mmol) 2-amino-pyridine (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M=308.41, found mass $M^+$=308.1

Example 2

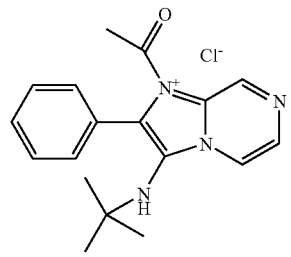

1-acetyl-3-tert-butylamino-2-phenyl-imidazo[1,2-a]-pyrazin-1-ium chloride

Example 2 was carried out in accordance with the general directions for synthesis in process step a) from 1.0 ml (0.1 mmol) 2-amino-pyrazine (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M=309.35, found mass $M^+$=309.2

Example 3

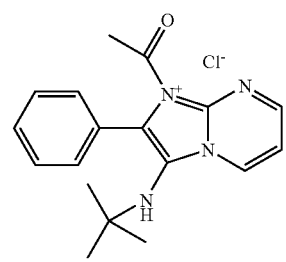

1-acetyl-3-tert-butylamino-2-phenyl-imidazo[1,2-a]-pyrimidin-1-ium chloride

Example 3 was carried out in accordance with the general directions for synthesis in process step a) from 1.0 ml (0.1 mmol) 2-amino-pyrimidine (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M=309.35, found mass $M^+$=309.2

Example 4

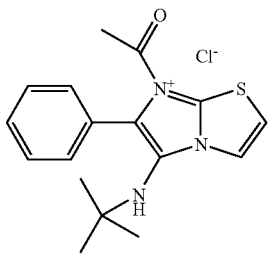

7-acetyl-5-tert-butylamino-6-phenyl-imidazo[2,1-b]-thiazol-7-ium chloride

Example 4 was carried out in accordance with the general directions for synthesis in process step a) from 1.0 ml (0.1 mmol) 2-amino-thiazole (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=314.39, found mass $M^+$=314.1

Example 5

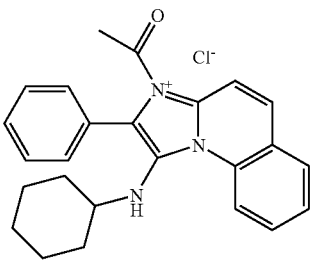

3-acetyl-1-cyclohexylamino-2-phenyl-imidazo[1,2-a]-quinolin-3-ium chloride

Example 5 was carried out in accordance with the general directions for synthesis in process step a) from 1.0 ml (0.1 mmol) 2-amino-quinoline (0.1 M, DCM), 0.575 ml (0.115 mmol) cyclohexylisonitrile solution (0.2 M, DCM), 0.500 ml (0.15 mmol) benzaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=419.96, found mass M−H=418.5

Example 6

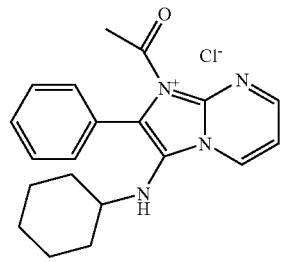

1-acetyl-3-cyclohexylamino-2-phenyl-imidazo[1,2-a]-pyrimidin-1-ium chloride

Example 6 was carried out in accordance with the general directions for synthesis in process step a) from 1.0 ml (0.1 mmol) 2-amino-pyrimidine (0.1 M, DCM), 0.575 ml (0.115 mmol) cyclohexylisonitrile solution (0.2 M, DCM), 0.500 ml (0.15 mmol) benzaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=335.39, found mass $M^+$=335.3

Example 7

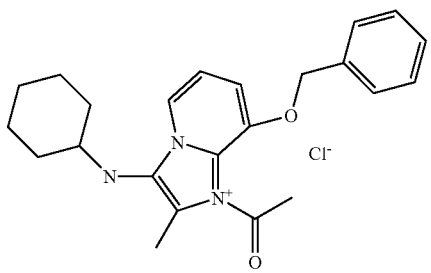

1-acetyl-8-benzyloxy-3-cyclohexylamino-2-methyl-imidazo[1,2-a]pyridin-1-ium chloride Example 7 was carried out in accordance with the general directions for synthesis in process step a) from 1.0 ml (0.1 mmol) 2-amino-3-benzyloxypyridine (0.1 M, DCM), 0.575 ml (0.115 mmol) cyclohexylisonitrile solution (0.2 M, DCM), 0.500 ml (0.15 mmol) acetaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=378.5, found mass $M^+$−acetyl=336.4

Example 8

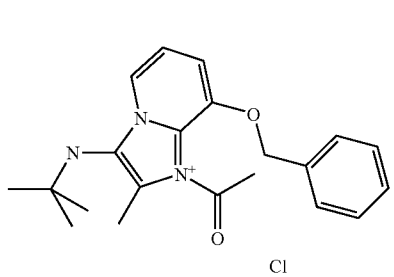

1-acetyl-8-benzyloxy-3-tert-butylamino-2-methyl-imidazo[1,2-a]pyridin-1-ium chloride Example 8 was carried out in accordance with the general directions for synthesis in process step a) from 1.0 ml (0.1 mmol) 2-amino-3-benzyloxypyridine (0.1 M, DCM), 0.575 ml (0.115 mmol) tert.-butylisonitrile solution (0.2 M, DCM), 0.500 ml (0.15 mmol) acetaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=352.46, found mass M$^+$–acetyl=310.3

Example 9

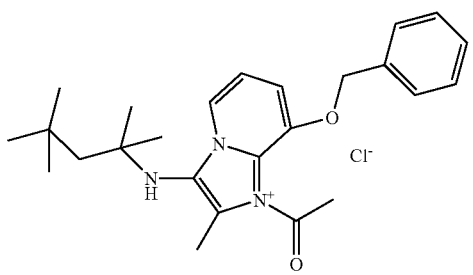

1-acetyl-8-benzyloxy-2-methyl-3-(1,1,3,3-tetramethylbutylamino)imidazo[1,2-a]pyridin-1-ium chloride Example 9 was carried out in accordance with the general directions for synthesis in process step a) from 1.0 ml (0.1 mmol) 2-amino-3-benzyloxypyridine (0.1 M, DCM), 0.575 ml (0.115 mmol) 1,1,3,3-tetramethylbutylisonitrile solution (0.2 M, DCM), 0.500 ml (0.15 mmol) acetaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M=408.57, found mass M$^+$–acetyl=366.0

Example 10

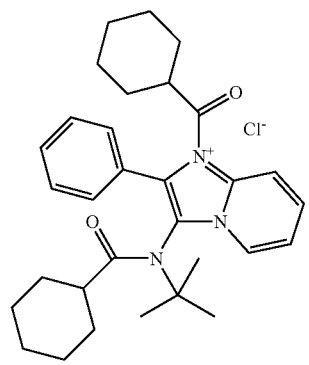

3-(tert-butyl-cyclohexancarbonyl-amino)-1-cyclohexancarbonyl-2-phenyl-imidazo[1,2-a]pyridin-1-ium chloride Example 10 was carried out in accordance with the general directions for synthesis in process step a) from 1.0 ml (0.1 mmol) 2-amino-pyridine (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 µl perchloric acid (w=20%) and in process steps b) to d) by reacting the resultant reaction product with 0.4 mmol cyclohexylcarboxylic acid chloride.

Characterization by ESI-MS, calculated mass M–Cl$^-$=486.68, found mass M$^+$=486.3

Example 11

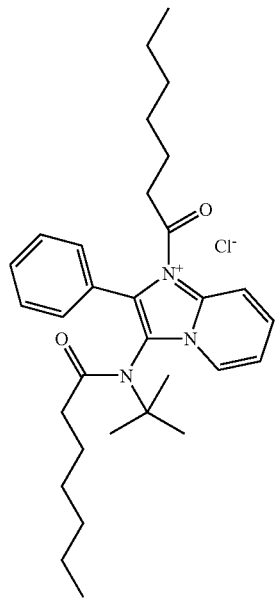

3-(tert-butyl-heptanoyl-amino)-1-heptanoyl-2-phenyl-imidazo[1,2-a]pyridin-1-ium chloride Example 11 was carried out in accordance with the general directions for synthesis in process step a) from 1.0 ml (0.1 mmol) 2-amino-pyridine (0.1 M, DCM), 0.575 ml (0.115 mmol) tert.-butylisonitrile solution (0.2 M, DCM), 0.500 ml (0.15 mmol) benzaldehyde solution (0.3 M, DCM) and 10 µl perchloric acid (w=20%) and in process steps b) to d) by reacting the resultant reaction product with 0.4 mmol heptylcarboxylic acid chloride.

Characterization by ESI-MS, calculated mass M−Cl⁻ =490.72, found mass M⁺=490.3

Example 12

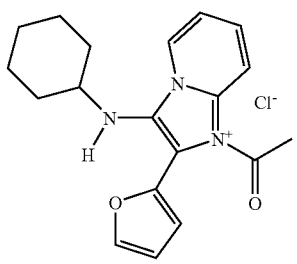

1-acetyl-3-cyclohexylamino-2-furan-2-yl-imidazo[1,2-a]pyridin-1-ium chloride

Example 12 was carried out in accordance with the general directions for synthesis in process step a) from 1.0 ml (0.1 mmol) 2-amino-pyridine (0.1 M, DCM), 0.575 ml (0.115 mmol) cyclohexylisonitrile solution (0.2 M, DCM), 0.500 ml (0.15 mmol) furfural solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =324.41, found mass M⁺=324.3

Example 13

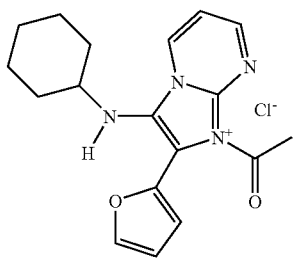

1-acetyl-3-cyclohexylamino-2-furan-2-yl-imidazo[1,2-a]pyrimidin-1-ium chloride

Example 13 was carried out in accordance with the general directions for synthesis in process step a) from 1.0 ml (0.1 mmol) 2-amino-pyrimidine (0.1 M, DCM), 0.575 ml (0.115 mmol) cyclohexylisonitrile solution (0.2 M, DCM), 0.500 ml (0.15 mmol) furfural solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =325.39, found mass M⁺=325.3

Example 14

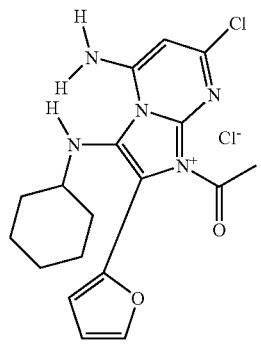

1-acetyl-5-amino-7-chloro-3-cyclohexylamino-2-furan-2-yl-imidazo[1,2-a]pyrimidin-1-ium chloride Example 14 was carried out in accordance with the general directions for synthesis in process step a) from 1.0 ml (0.1 mmol) 2,6-diamino-4-chloropyrimidine (0.1 M, DCM), 0.575 ml (0.115 mmol) cyclohexylisonitrile solution (0.2 M, DCM), 0.500 ml (0.15 mmol) furfural solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =374.85, found mass M⁺=374.5

Example 15

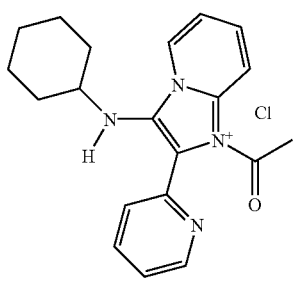

1-acetyl-3-cyclohexylamino-2-pyridin-2-yl-imidazo[1,2-a]pyridin-1-ium chloride

Example 15 was carried out in accordance with the general directions for synthesis in process step a) from 1.0 ml (0.1 mmol) 2-amino-pyridine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =335.42, found mass M⁺=335.4

Example 16

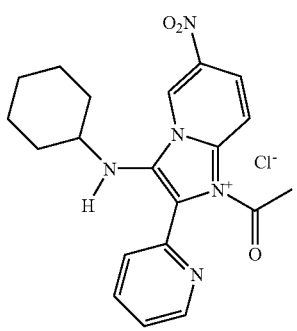

1-acetyl-3-cyclohexylamino-6-nitro-2-pyridin-2-yl-imidazo[1,2-a]pyridin-1-ium chloride Example 16 was carried out in accordance with the general directions for synthesis in process step a) from 1.0 ml (0.1 mmol) 2-amino-5-nitropyridine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl$^-$=380.43, found mass M$^+$=380.3

Example 17

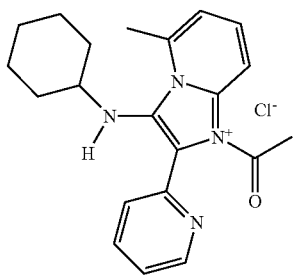

1-acetyl-3-cyclohexylamino-5-methyl-2-pyridin-2-yl-imidazo[1,2-a]pyridin-1-ium chloride Example 17 was carried out in accordance with the general directions for synthesis in process step a) from 1.0 ml (0.1 mmol) 2-amino-6-methylpyridine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 ill perchloric acid (w=20%) and in process step c) and d) by reacting the resultant reaction product with 0.4 mmol acetylchloride.

Characterization by ESI-MS, calculated mass M–Cl$^-$=349.46, found mass M$^+$=349.4

Example 18

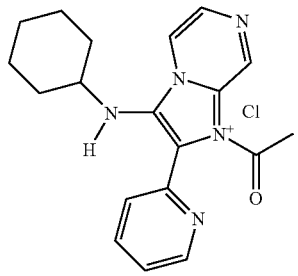

1-acetyl-3-cyclohexylamino-2-pyridin-2-yl-imidazo[1,2-a]pyrazin-1-ium chloride

Example 18 was carried out in accordance with the general directions for synthesis in process step a) from 1.0 ml (0.1 mmol) 2-amino-pyrazine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl$^-$=336.42, found mass M$^+$=336.3

Example 19

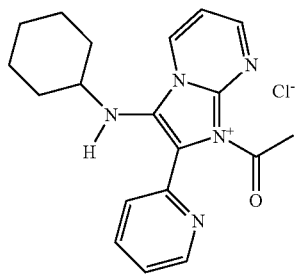

1-acetyl-3-cyclohexylamino-2-pyridin-2-yl-imidazo[1,2-a]pyrimidin-1-ium chloride Example 19 was carried out in accordance with the general directions for synthesis in process step a) from 1.0 ml (0.1 mmol) 2-amino-pyrimidine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl$^-$=336.42, found mass M$^+$=336.3

Example 20

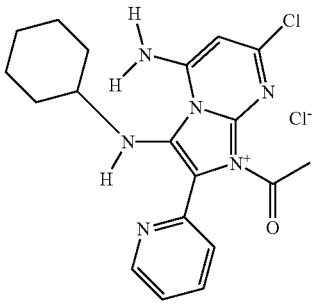

1-acetyl-5-amino-7-chloro-3-cyclohexylamino-2-pyridin-2-yl-imidazo[1,2-a]pyrimidin-1-ium chloride Example 20 was carried out in accordance with the general directions for synthesis in process step a) from 1.0 ml (0.1 mmol) 2,6-diamino-4-chloro-pyrimidine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μL perchloric acid (w=20%) and in process step c) and d) by reacting the resultant reaction product with 0.4 mmol acetylchloride.

Characterization by ESI-MS, calculated mass M–Cl[31] =336.42, found mass M+=336.3

Example 21

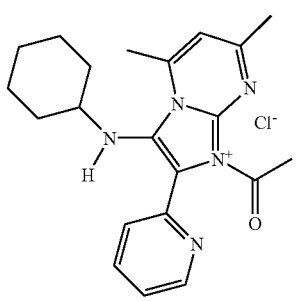

1-acetyl-3-cyclohexylamino-5,7-dimethyl-2-pyridin-2-yl-imidazo[1,2-a]pyrimidin-1-ium chloride Example 21 was carried out in accordance with the general directions for synthesis in process step a) from 1.0 ml (0.1 mmol) 2-amino-4,6-dimethylpyrimidine (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl− =364.47, found mass M+=364.4

Example 22

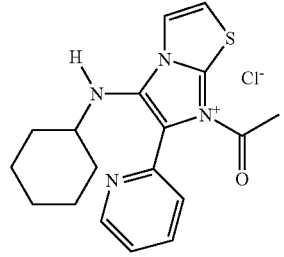

7-acetyl-5-cyclohexylamino-6-pyridin-2-yl-imidazo[2,1-b]thiazol-7-ium chloride

Example 22 was carried out in accordance with the general directions for synthesis in process step a) from 1.0 ml (0.1 mmol) 2-aminothiazole (0.1 M, DCM), 0.575 ml (0.115 mmol) cyclohexylisonitrile solution (0.2 M, DCM), 0.500 ml (0.15 mmol) pyridine-2-carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl− =341.46, found mass M+=341.2

Example 23

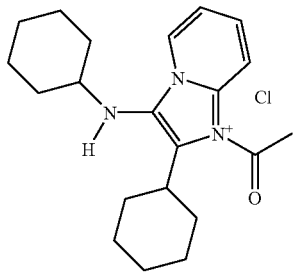

1-acetyl-2-cyclohexyl-3-cyclohexylamino-imidazo[1,2-a]pyridin-1-ium chloride

Example 23 was carried out in accordance with the general directions for synthesis in process step a) from 1.0 ml (0.1 mmol) 2-amino-pyridine (0.1 M, DCM), 0.575 ml (0.115 mmol) cyclohexylisonitrile solution (0.2 M, DCM), 0.500 ml (0.15 mmol) cyclohexane carbaldehyde solution (0.3 M, DCM) and 10 μl perchloric acid (w=20%) and in process step c) and d) by reacting the resultant reaction product with 0.4 mmol acetylchloride.

Characterization by ESI-MS, calculated mass M–Cl− =340.49, found mass M+=340.5

Example 24

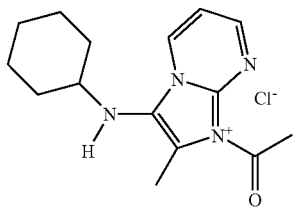

1-acetyl-3-cyclohexylamino-2-methyl-imidazo[1,2-a]pyrimidin-1-ium chloride

Example 24 was carried out in accordance with the general directions for synthesis in process step a) from 1.0 ml (0.1 mmol) 2-amino-pyrimidine (0.1 M, DCM), 0.575 ml (0.115 mmol) cyclohexylisonitrile solution (0.2 M, DCM), 0.500 ml (0.15 mmol) acetaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M–Cl⁻ =273.63, found mass $M^+$=272.3

Example 25

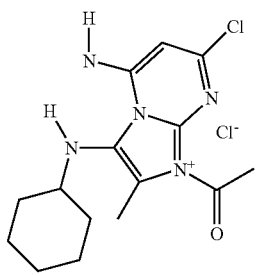

1-acetyl-5-amino-7-chloro-3-cyclohexylamino-2-methyl-imidazo[1,2-a]pyrimidin-1-ium chloride Example 25 was carried out in accordance with the general directions for synthesis in process step a) from 1.0 ml (0.1 mmol) 2,6-diamino-4-chloro-pyrimidine (0.1 M, DCM), 0.575 ml (0.115 mmol) cyclohexylisonitrile solution (0.2 M, DCM), 0.500 ml (0.15 mmol) acetaldehyde solution (0.3 M, DCM) and 10 µL perchloric acid (w=20%) and in process step c) and d) by reacting the resultant reaction product with 0.4 mmol acetylchloride.

Characterization by ESI-MS, calculated mass M–Cl⁻ =322.82, found mass $M^+$=322.3

Example 26

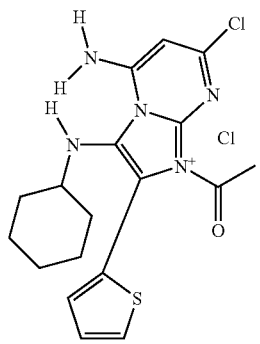

1-acetyl-5-amino-7-chloro-3-cyclohexylamino-2-thiophene-2-yl-imidazo[1,2-a]pyrimidin-1-ium chloride Example 26 was carried out in accordance with the general directions for synthesis in process step a) from 1.0 ml (0.1 mmol) 2,6-diamino-4-chloro-pyrimidine (0.1 M, DCM), 0.575 ml (0.115 mmol) cyclohexylisonitrile solution (0.2 M, DCM), 0.500 ml (0.15 mmol) thiophene-2-carbaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M–Cl⁻ =322.82, found mass $M^+$=322.3

Example 27

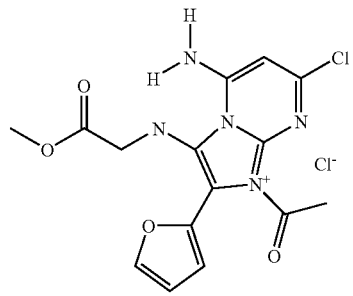

1-acetyl-5-amino-7-chloro-2-furan-2-yl-3-(methoxycarbonylmethylamino)imidazo[1,2-a]pyrimidin-1-ium chloride Example 27 was carried out in accordance with the general directions for synthesis in process step a) from 1.0 ml (0.1 mmol) 2,6-diamino-4-chloro-pyrimidine (0.1 M, DCM), 0.575 ml (0.115 mmol) isocyanoacetic acid methyl ester solution (0.2 M, DCM), 0.500 ml (0.15 mmol) furfural solution (0.3 M, DCM) and 10 µl perchloric acid (w=20%) and in process step c) and d) by reacting the resultant reaction product with 0.4 mmol acetylchloride.

Characterization by ESI-MS, calculated mass M–Cl⁻ =364.77, found mass $M^+$=364.5

Example 28

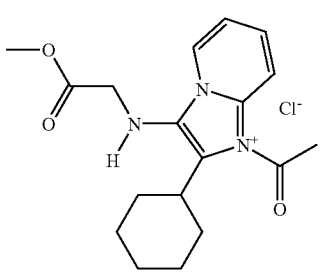

1-acetyl-2-cyclohexyl-3-(methoxycarbonylmethylamino)imidazo[1,2-a]pyridin-1-ium chloride Example 28 was carried out in accordance with the general directions for synthesis in process step a) from 1.0 ml (0.1 mmol) 2-amino-pyridine (0.1 M, DCM), 0.575 ml (0.115 mmol) isocyanoacetic acid methyl ester solution (0.2 M, DCM), 0.500 ml (0.15 mmol) cyclohexylcarbaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =330.41, found mass M⁺=330.4

Example 29

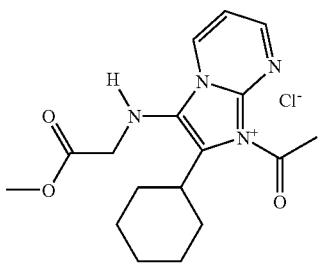

1-acetyl-2-cyclohexyl-3-(methoxycarbonylmethylamino)imidazo[1,2-a]pyrimidin-1-ium chloride Example 29 was carried out in accordance with the general directions for synthesis in process step a) from 1.0 ml (0.1 mmol) 2-amino-pyrimidine (0.1 M, DCM), 0.575 ml (0.115 mmol) isocyanoacetic acid methyl ester solution (0.2 M, DCM), 0.500 ml (0.15 mmol) cyclohexylcarbaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =331.40, found mass M⁺=331.3

Example 30

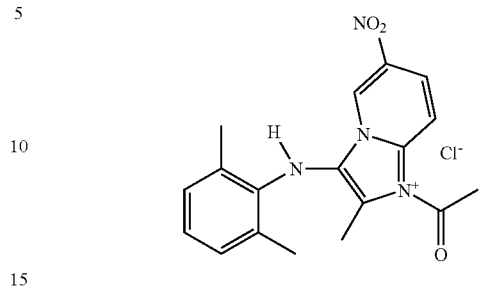

1-acetyl-3-(2,6-dimethyl-phenylamino)-2-methyl-6-nitro-imidazo pyridin-1-ium chloride Example 30 was carried out in accordance with the general directions for synthesis in process step a) from 1.0 ml (0.1 mmol) 2-amino-5-nitropyridine (0.1 M, DCM), 0.575 ml (0.115 mmol) 2,6-dimethylphenylisocyanide solution (0.2 M, DCM), 0.500 ml (0.15 mmol) acetaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =339.38, found mass M⁺=339.0

Example 31

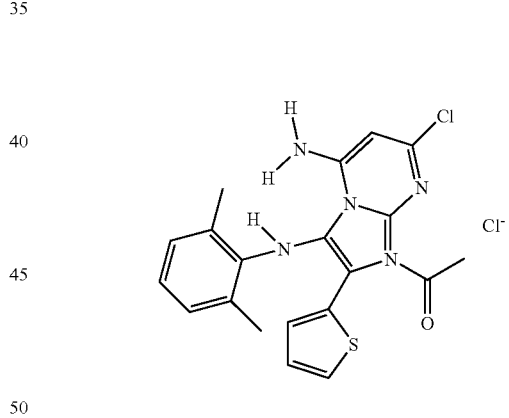

1-acetyl-5-amino-7-chloro-3-(2,6-dimethyl-phenylamino)-2-thiophene-2-yl-imidazo[1,2-a]pyrimidin-1-ium chloride Example 31 was carried out in accordance with the general directions for synthesis in process step a) from 1.0 ml (0.1 mmol) 2,6-diamino-4-chloropyridine (0.1 M, DCM), 0.575 ml (0.115 mmol) 2,6-dimethylphenylisocyanide solution (0.2 M, DCM), 0.500 ml (0.15 mmol) thiophene-2-carbaldehyde solution (0.3 M, DCM) and 10 µl perchloric acid (w=20%) and in process step c) and d) by reacting the resultant reaction product with 0.4 mmol acetylchloride.

Characterization by ESI-MS, calculated mass M−Cl⁻ =412.92, found mass M⁺=412.2

Example 32

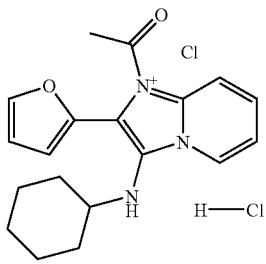

1-acetyl-3-cyclohexylamino-2-furan-2-yl-imidazo[1,2-a]pyridin-1-ium chloride hydrochloride 655 mg (6.1 mmol) 5-methyl-2-aminopyridin were placed in 12 ml methanol, and 874 mg (0.75 ml; 9.1 mmol) furan-2-carbaldehyde, 768 mg (0.86 ml; 7.0 mmol) cyclohexylisonitrile and 0.59 ml aqueous perchloric acid (20 m %) were then added and stirred at ambient temperature for 22 hours. 50 ml water and 40 ml DCM were added for processing purposes, stirred for 10 minutes, and the phases then separated. The aqueous phase was additionally extracted three times with 20 ml DCM in each case and the combined organic phases then shaken briefly with 50 ml saturated sodium chloride solution, separated off, dried over magnesium sulphate, filtered and concentrated under vacuum. The intermediate product obtained (1.83 g; 6.2 mmol) was dissolved in 10 ml DCM, and four equivalents acetyl chloride (24.8 mmol; 1.8 ml) were added dropwise while stirring at 20° C. and were stirred for a further four hours. The reaction mixture was then concentrated under vacuum and dried in an oil pump vacuum. The untreated product (about 2 g) was dissolved in 15.5 ml 2-butanone, 51 µl water and 0.72 ml trimethylchlorosilane were added and the mixture was stirred overnight. The precipitated HCl adduct of 1-acetyl-3-cyclohexylamino-2-furan-2-yl-imidazo[1,2-a]pyridin-1-ium chloride was suction-filtered and dried under vacuum. 776 mg 1-acetyl-3-cyclohexylamino-2-furan-2-yl-imidazo[1,2-a]pyridin-1-ium chloride hydrochloride were obtained.

Characterization by 300 MHz $^1$H-NMR spectroscopy (no detectable impurities).

Pharmacological Investigations:

µ-Opiate Receptor Binding Investigations

Investigations to determine the affinity of the compounds of Formula I according to the invention for the i-opiate receptor were carried out on brain membrane homogenates (homogenate of rat brain without cerebellum, pons and medulla oblongata of male Wistar rats).

For this purpose, the respective freshly prepared rat brain was homogenized in 50 mmol/l tris-HCl (pH 7.4) with ice cooling and was centrifuged for 10 minutes at 5,000 g and 4° C. After decanting and rejection of the supernatant, retrieval and homogenisation of the membrane sediment in 50 mmol/l tris-HCl (pH 7.4), the homogenate was then centrifuged for 20 minutes at 20,000 g and 4° C. This washing stage was repeated several times. The supernatant was then decanted and the membrane sediment homogenized in cold 50 mmol/l tris-HCl, 20% glycerol (w/v), 0.01% Bactitracin (w/v) (pH 7.4) and frozen in aliquots until testing. To test receptor binding, the aliquots were thawed and diluted 1:10 with the binding test buffer.

In the binding test, a 50 mmol/l tris-HCl, 5 mmol/l MgCl (pH 7.4) was used as buffer and 1 nmol/l tritiated naloxone as radioactive ligand.

| Compound according to invention | µ-affinity % inhibition 10 µM |
|---|---|
| Example 4 | 90 |
| Example 5 | 79 |
| Example 6 | 53 |
| Example 7 | 91 |
| Example 8 | 98 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

We claim:

1. A salt of a bicyclic, N-acylated imidazo-3-amine or an imidazo-5-amine of Formula I:

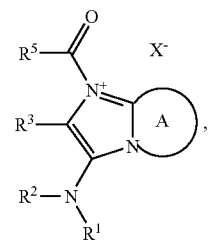

wherein
R$^1$ is tert-butyl; 1,1,3,3-tetramethylbutyl; (CH$_2$)$_n$CN where n=4, 5 or 6; optionally substituted phenyl; C$_4$–C$_8$ cycloalkyl; CH$_2$CH$_2$R where R=4-morpholino; or CH$_2$R$^a$,
  wherein R$^a$ represents hydrogen; straight or branched C$_1$–C$_8$ alkyl; optionally substituted phenyl; CO(OR') where R'=straight or branched C$_1$–C$_8$ alkyl; PO(OR'')$_2$ where R''=straight or branched C$_1$–C$_4$ alkyl; or Si(R$^x$R$^y$R$^z$) where R$^x$, R$^y$, and R$^z$ each independently is straight or branched C$_1$–C$_4$ alkyl, C$_4$–C$_8$ cycloakyl or phenyl,
R$^2$ is hydrogen; COR$^b$, wherein R$^b$ is straight or branched C$_1$–C$_8$ alkyl; straight or branched C$_1$–C$_8$ alkoxy; C$_3$–C$_8$ cycloalkyl; CH$_2$CH$_2$CO(OR') where R'=straight or branched C$_1$–C$_4$ alkyl; adamantyl; optionally substituted phenyl; benzyloxy; optionally substituted 1-naphthyl or 2-naphthyl or respectively optionally substituted 2-pyridyl, 3-pyridyl, 4-pyridyl, thiazolyl or furyl; CH$_2$R$^c$, wherein R$^c$ is hydrogen, straight or branched C$_1$–C$_8$ alkyl or optionally substituted phenyl; CH$_2$CH$_2$R$^d$, wherein R$^d$ is optionally substituted phenyl; or CONHR$^e$,
  wherein R$^e$ is branched or straight C$_1$–C$_8$ alkyl; aryl; heteroaryl; C$_3$–C$_8$ cycloalkyl or an aryl bound via a C$_1$–C$_3$ alkylene group, heteroaryl or C$_3$–C$_8$ cycloalkyl radical, $R^3$ is straight or branched $C_1$–$C_8$ alkyl; $C_3$–$C_8$ cycloalkyl; optionally substituted phenyl; optionally substituted 1-naphthyl; 2-naphthyl; quinoline; anthracene; phenanthrene; benzothiophene; benzofurfuryl; optionally substituted pyrrole; 2-, 3- or 4-pyridyl; optionally substituted furfuryl; or optionally substituted thiophene, A is a four-membered ring fragment of the formula:

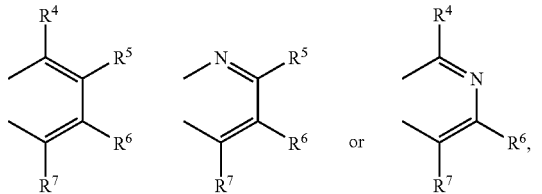

wherein $R^4$, $R^5$, $R^6$ and $R^7$ each independently is hydrogen; straight or branched $C_1$–$C_8$ alkyl; fluorine; chlorine; bromine; $CF_3$; CN; $NO_2$; $NHR^f$,
wherein $R^f$ represents hydrogen; straight or branched $C_1$–$C_8$ alkyl; or $COR'''$ wherein $R'''$=straight or branched $C_1$–$C_4$ alkyl or optionally substituted phenyl;

$SR^g$,
wherein $R^g$ represents hydrogen, straight or branched $C_1$–$C_4$ alkyl, optionally substituted phenyl, optionally substituted pyridine, optionally substituted benzyl, or optionally substituted fluorenyl;

$OR^h$,
wherein $R^h$ represents hydrogen; straight or branched $C_1$–$C_8$ alkyl; $COR'''$ where $R'''$=straight or branched $C_1$–$C_4$ alkyl or optionally substituted phenyl; or CO(OR') wherein R'=straight or branched $C_1$–$C_8$ alkyl;

CO($OR^i$) or $CH_2$CO($OR^i$), wherein $R^i$ is branched or straight $C_1$–$C_8$ alkyl, or optionally substituted phenyl;

or $R^6$ and $R^7$ together represent a ring fragment —$CR^i$=$CR^j$—CH=CH—, wherein $R^i$ and $R^j$ each represents hydrogen, or one of $R^i$ and $R^j$ is not hydrogen and represents F, Cl, Br, I or straight or branched $C_1$–$C_8$ alkyl, whereas $R^4$ and $R^5$ independently thereof have the meaning given above, $R^8$ is branched or straight $C_1$–$C_8$ alkyl; aryl; heteroaryl; $C_3$–$C_8$ cycloalkyl; or an aryl bound by a $C_1$–$C_3$ alkylene group, heteroaryl or $C_3$–$C_8$ cycloalkyl radical, and X represents an anion of an inorganic or organic acid.

2. A salt according to claim 1, wherein $R^2$ is hydrogen, $R^1$ is selected from the group consisting of $(CH_2)_6$CN, cyclohexyl, $CH_2$CO(Omethyl), 2,6-dimethylphenyl, tert-butyl and $CH_2CH_2$R(R=4-morpholino), and $R^3$ is selected from the group consisting of 4-acetamidophenyl, 2-bromophenyl, 3-bromophenyl, 4-bromophenyl, 4-bromo-2-fluorophenyl, 5-bromo-2-fluorophenyl, 3-bromo-4-fluorophenyl, 4-tert. butylphenyl, 2-chloro-4-fluorophenyl, 2-chloro-6-fluorophenyl, 2-chlorophenyl, 3-chlorophenyl, 4-chlorophenyl, 4-cyanophenyl, 2,3-dichlorophenyl, 2,4-dichlorophenyl, 3,4-dichlorophenyl, 2,3-dimethoxyphenyl, 3,4-dimethoxyphenyl, 2,4-dimethylphenyl, 2,5-dimethylphenyl, 2-fluorophenyl, 3-fluorophenyl, 4-fluorophenyl, 4-hexylphenyl, 3-hydroxyphenyl, 2-methoxyphenyl, 2-methylphenyl, 3-methylphenyl, 4-methylphenyl, 4-nitrophenyl, 3-phenoxyphenyl, 4-(1-pyrrolidino)-phenyl, 2-(trifluoromethyl)phenyl, 3-(trifluoromethyl)phenyl, 4-(trifluoromethyl)-phenyl, 3,4,5-trimethoxyphenyl, 3-(4-chlorophenoxy)phenyl, 4-acetoxy-3-methoxyphenyl, 4-dimethylaminonaphthyl, 2-ethoxynaphthyl, 4-methoxynaphthyl, 2-(1-(phenylsulfonyl)-pyrrole), 2-(N-methylpyrrole), 2-(N-(3,5-dichlorophenyl)pyrrole), 2-(1-(4-chlorophenyl)pyrrole), 2-(5-acetoxymethylfurfuryl), 2-(5-methylfurfuryl), 2-(5-nitrofurfuryl), 2-[5-(3-nitrophenyl)furfuryl], 2-[5-(2-nitrophenyl)furfuryl], 2-(5-bromofurfuryl), 2-[5-(4-chlorophenyl)furfuryl], 2-(4,5-dimethylfurfuryl), 2-[5-(2-chlorophenyl)furfuryl], 2-(5-ethylfurfuryl), 2-[5-(1,3-dioxalanfurfuryl], 2-(5-chlorothiophenyl), 2-(5-methylthiophenyl), 2-(5-ethylthiophenyl), 2-(3-methylthiophenyl), 2-(4-bromothiophenyl), 2-(5-nitrothiophenyl), 5-(2-carboxylic acid thiophenyl), 2-[4-(phenylethyl)-thiophenyl], 2-[5-(methylthio)thiophenyl], 2-(3-bromothiophenyl), 2-(3-phenoxythiophenyl) and 2-(5-bromothiophenyl).

3. A salt according to claim 1, wherein $R^3$ is selected from the group consisting of methyl, cyclohexyl, phenyl, furan-2-yl, 2-pyridyl and 2-thiophenyl.

4. A salt according to claim 1, wherein $R^4$, $R^5$, $R^6$ and $R^7$ are selected, independently from one another, from the group consisting of hydrogen; methyl; ethyl; isopropyl; n-propyl; n-butyl; fluorine; bromine; $CF_3$; CN; $NO_2$; $NHR^f$, wherein $R^f$ represents hydrogen, methyl, ethyl, n-propyl, n-butyl, C(O)methyl or C(O)phenyl; $SR^g$, wherein $R^g$ represents hydrogen, methyl, ethyl, n-propyl; n-butyl, or phenyl; $OR^h$, wherein $R^h$ represents hydrogen, methyl, ethyl, n-propyl, n-butyl, or phenyl; C°methyl; C°phenyl; CO(Omethyl); CO(Oethyl); and CO($OR^i$) or $CH_2$CO($OR^i$), wherein $R^i$ represents methyl, ethyl, n-propyl, n-butyl or phenyl.

5. A salt according to claim 4, wherein $R^4$, $R^5$, $R^6$ and $R^7$ are selected independently from one another, from the group consisting of hydrogen, methyl, chlorine, $NH_2$ and $NO_2$.

6. A salt according to claim 1, wherein $R^8$ is methyl; ethyl; n-propyl; n-butyl; n-pentyl; n-hexyl; phenyl; cycolhexyl; or 2-naphthyl unsubstituted, monosubstituted in the 4-position or disubstituted in the 2- and 6-positions.

7. A salt according to claim 6, wherein $R^8$ is methyl, n-hexyl, 2,6-dichlorophenyl, 4-methoxyphenyl, cyclohexyl or 2-naphthyl.

8. A salt according to claim 1, wherein X is an anion of hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid or aspartic acid.

9. A salt according to claim 8, wherein X is an anion of hydrochloric acid.

10. A salt according to claim 1, wherein the salt is provided in the form of an addition product with an acid.

11. An addition product according to claim 10, wherein the acid is a physiologically acceptable acid.

12. A salt according to claim 1, wherein the salt is selected from the group consisting of:
1-acetyl-3-tert-butylamino-2-phenyl-imidazo[1,2-a]-pyridin-1-ium chloride,
1-acetyl-3-tert-butylamino-2-phenyl-imidazo[1,2-a]-pyrazin-1-ium chloride,
1-acetyl-3-tert-butylamino-2-phenyl-imidazo[1,2-a]-pyrimidin-1-ium chloride,
3-acetyl-1-cyclohexylamino-2-phenyl-imidazo[1,2-a]-quinolin-3-ium chloride, 1-acetyl-3-cyclohexylamino-2-phenyl-imidazo[1,2-a]-pyrimidin-1-ium chloride,
1-acetyl-8-benzyloxy-3-cyclohexylamino-2-methyl-imidazo[1,2-a]pyridin-1-ium chloride,
1-acetyl-8-benzyloxy-3-tert-butylamino-2-methyl-imidazo[1,2-a]pyridin-1-ium chloride,
1-acetyl-8-benzyloxy-2-methyl-3-(1, 1, 3, 3-tetramethyl-butylamino)imidazo[1,2-a]pyridin-1-ium chloride,
3-(tert-butyl-cyclohexancarbonyl-amino)-1-cyclohexancarbonyl-2-phenyl-imidazo[1,2-a]pyridin-1-ium chloride,
3-(tert-butyl-heptanoyl-amino)-1-heptanoyl-2-phenyl-imidazo[1,2-a]pyridin-1-ium chloride,
1-acetyl-3-cyclohexylamino-2-furan-2-yl-imidazo[1,2-a]pyridin-1-ium chloride,
1-acetyl-3-cyclohexylamino-2-furan-2-yl-imidazo[1,2-a]pyrimidin-1-ium chloride,
1-acetyl-5-amino-7-chloro-3-cyclohexylamino-2-furan-2-yl-imidazo[1,2-a]pyrimidin-1-ium chloride,
1-acetyl-3-cyclohexylamino-2-pyridin-2-yl-imidazo[1,2-a]pyridin-1-ium chloride,
1-acetyl-3-cyclohexylamino-6-nitro-2-pyridin-2-yl-imidazo[1,2-a]pyridin-1-ium chloride,
1-acetyl-3-cyclohexylamino-5-methyl-2-pyridin-2-yl-imidazo[1,2-a]pyridin-1-ium chloride,
1-acetyl-3-cyclohexylamino-2-pyridin-2-yl-imidazo[1,2-a]pyrazin-1-ium chloride,
1-acetyl-3-cyclohexylamino-2-pyridin-2-yl-imidazo[1,2-a]pyrimidin-1-ium chloride,
1-acetyl-5-amino-7-chloro-3-cyclohexylamino-2-pyridin-2-yl-imidazo[1,2-a]pyrimidin-1-ium chloride,
1-acetyl-3-cyclohexylamino-5,7-dimethyl-2-pyridin-2-yl-imidazo[1,2-a]pyrimidin-1-ium chloride,
1-acetyl-2-cyclohexyl-3-cyclohexylamino-imidazo[1,2-a]pyridin-1-ium chloride,
1-acetyl-3-cyclohexylamino-2-methyl-imidazo[1,2-a]pyrimidin-1-ium chloride,
1-acetyl-5-amino-7-chloro-3-cyclohexylamino-2-methyl-imidazo[1,2-a]pyrimidin-1-ium chloride,
1-acetyl-5-amino-7-chloro-3-cyclohexylamino-2-thiophene-2-yl-imidazo[1,2-a]pyrimidin-1-ium chloride,
1-acetyl-5-amino-7-chloro-2-furan-2-yl-3-(methoxycarbonylmethylamino) imidazo[1,2-a]pyrimidin-1-ium chloride,
1-acetyl-2-cyclohexyl-3-(methoxycarbonylmethylamino) imidazo[1,2-a]pyridin-1-ium chloride,
1-acetyl-2-cyclohexyl-3-(methoxycarbonylmethylamino) imidazo[1,2-a]pyrimidin-1-ium chloride,
1-acetyl-3-(2,6-dimethyl-phenylamino)-2-methyl-6-nitro-imidazo[1,2-a]pyridin-1-ium chloride,
1-acetyl-5-amino-7-chloro-3-(2,6-dimethyl-phenylamino)-2-thiophene-2-yl-imidazo[1,2-a]pyrimidin-1-ium chloride, and
1-acetyl-3-cyclohexylamino-2-furan-2-yl-imidazo[1,2-a]pyridin-1-ium chloride hydrochloride.

13. A process for producing a salt of a bicyclic, N-acylated imidazo-3-amine or of an imidazo-5-amine of Formula I according to claim 1, the process comprising the steps of:
a) producing an imidazo-3-amine or an imidazo-5-amine by a three-component reaction from starting compounds consisting of an amidine, aldehyde and isonitrile in a solvent, in the presence of an acid, wherein the starting compounds are added in succession in the sequence amidine, aldehyde and isonitrile, toから a first product, b) optionally for producing compounds in which $R^2$ is not hydrogen, reacting the first product formed in step a) with a compound $R^2$Hal, wherein Hal is bromine, iodine or chlorine, or with an isocyanate, to produce a second product,
c) reacting the first product from step a) or the second product from step b) with a molar excess of an acid chloride $R^8C(O)Cl$, whereby a reaction mixture is formed,
d) on completion of reaction in step c), removing excess acid chloride from the reaction mixture, and
e) optionally exchanging the chloride for a different acid radical.

14. A process according to claim 13, wherein the solvent in step a) is dichloromethane.

15. A process according to claim 13, wherein the acid in step a) is perchloric acid.

16. A process according to claim 13, wherein Hal in step b) is chlorine.

17. A process according to claim 13, wherein in step c) the acid chloride is used in at least quadruple molar excess.

18. A process according to claim 13, wherein the acid radical in step e) is a radical of an acid selected from the group consisting of hydrobromic acid, sulphuric acid, methane sulphonic acid, formic acid, acetic acid, oxalic acid, succinic acid, tartaric acid, mandelic acid, fumaric acid, lactic acid, citric acid, glutamic acid and aspartic acid.

19. A process for producing an acid addition product of a salt of a bicyclic, N-acylated imidazo-3-amine or of an imidazo-5-amine, the process comprising the steps of:
i) producing the salt according to the process of claim 13, and
ii) treating the salt with an acid to produce an acid addition product.

20. A process according to claim 19, wherein the acid in step ii) is a physiologically acceptable acid.

21. A process according to claim 13, wherein process step c) is carried out in an ether or halogenated hydrocarbon solvent at a temperature of 0 to 60° C.

22. A process according to claim 21, wherein the ether is THF, or the halogenated hydrocarbon is DCM.

23. A process according to claim 13, wherein process step d) takes place 2 to 12 hours after addition of the acid chloride in process step c).

24. A process according to claim 13, wherein in process step d) the excess acid chloride is removed using a scavenger resin.

25. A process according to claim 24, wherein the scavenger resin is tris-(2-aminoethyl)amine polystyrene.

26. A pharmaceutical composition comprising at least one salt of a bicyclic, N-acylated imidazo-3-amine or an imidazo-5-amine according to claim 1, or at least one addition product thereof with a physiologically acceptable acid, and a pharmaceutically acceptable excipient.

27. A pharmaceutical composition according to claim 26, wherein the salt or an acid addition product thereof is selected from the group consisting of
1-acetyl-3-tert-butylamino-2-phenyl-imidazo[1,2-a]-pyridin-1-ium chloride,
1-acetyl-3-tert-butylamino-2-phenyl-imidazo[1,2-a]-pyrazin-1-ium chloride,
1-acetyl-3-tert-butylamino-2-phenyl-imidazo[1,2-a]-pyrimidin-1-ium chloride,
3-acetyl-1-cyclohexylamino-2-phenyl-imidazo[1,2-a]-quinolin-3-ium chloride,
1-acetyl-3-cyclohexylamino-2-phenyl-imidazo[1,2-a]-pyrimidin-1-ium chloride, 1-acetyl-8-benzyloxy-3-cyclohexylamino-2-methyl-imidazo[1,2-a]pyridin-1-ium chloride, 1-acetyl-8-benzyloxy-3-tert-butylamino-2-methyl-imidazo[1,2-a]pyridin-1-ium chloride, 1-acetyl-8-benzyloxy-2-methyl-3-(1,1,3,3-tetramethylbutylamino)imidazo[1,2-a]pyridin-1-ium chloride, 3-(tert-butyl-cyclohexancarbonyl-amino)-1-cyclohexancarbonyl-2-phenyl-imidazo[1,2-a]pyridin-1-ium chloride, 3-(tert-butyl-heptanoyl-amino)-1-heptanoyl-2-phenyl-imidazo[1,2-a]pyridin-1-ium chloride, 1-acetyl-3-cyclohexylamino-2-furan-2-yl-imidazo[1,2-a]pyridin-1-ium chloride, 1-acetyl-3-cyclohexylamino-2-furan-2-yl-imidazo[1,2-a]pyrimidin-1-ium chloride, 1-acetyl-5-amino-7-chloro-3-cyclohexylamino-2-furan-2-yl-imidazo[1,2-a]pyrimidin-1-ium chloride, 1-acetyl-3-cyclohexylamino-2-pyridin-2-yl-imidazo[1,2-a]pyridin-1-ium chloride, 1-acetyl-3-cyclohexylamino-6-nitro-2-pyridin-2-yl-imidazo[1,2-a]pyridin-1-ium chloride, 1-acetyl-3-cyclohexylamino-5-methyl-2-pyridin-2-yl-imidazo[1,2-a]pyridin-1-ium chloride, 1-acetyl-3-cyclohexylamino-2-pyridin-2-yl-imidazo[1,2-a]pyrazin-1-ium chloride, 1-acetyl-3-cyclohexylamino-2-pyridin-2-yl-imidazo[1,2-a]pyrimidin-1-ium chloride, 1-acetyl-5-amino-7-chloro-3-cyclohexylamino-2-pyridin-2-yl-imidazo[1,2-a]pyrimidin-1-ium chloride, 1-acetyl-3-cyclohexylamino-5,7-dimethyl-2-pyridin-2-yl-imidazo[1,2-a]pyrimidin-1-ium chloride, 1-acetyl-2-cyclohexyl-3-cyclohexylamino-imidazo[1,2-a]pyridin-1-ium chloride, 1-acetyl-3-cyclohexylamino-2-methyl-imidazo[1,2-a]pyrimidin-1-ium chloride, 1-acetyl-5-amino-7-chloro-3-cyclohexylamino-2-methyl-imidazo[1,2-a]pyrimidin-1-ium chloride, 1-acetyl-5-amino-7-chloro-3-cyclohexylamino-2-thiophene-2-yl-imidazo[1,2-a]pyrimidin-1-ium chloride, 1-acetyl-5-amino-7-chloro-2-furan-2-yl-3-(methoxycarbonylmethylamino)imidazo[1,2-a]pyrimidin-1-ium chloride, 1-acetyl-2-cyclohexyl-3-(methoxycarbonylmethylamino)imidazo[1,2-a]pyridin-1-ium chloride, 1-acetyl-2-cyclohexyl-3-(methoxycarbonylmethylamino)imidazo[1,2-a]pyrimidin-1-ium chloride, 1-acetyl-3-(2,6-dimethyl-phenylamino)-2-methyl-6-nitro-imidazo[1,2-a]pyridin-1-ium chloride, 1-acetyl-5-amino-7-chloro-3-(2,6-dimethyl-phenylamino)-2-thiophene-2-yl-imidazo[1,2-a]pyrimidin-1-ium chloride, and 1-acetyl-3-cyclohexylamino-2-furan-2-yl-imidazo[1,2-a]pyridin-1-ium chloride hydrochloride.

28. A method for the treatment of pain, comprising administering to a mammal in need thereof an effective amount of a pharmaceutical composition according to claim 26.

29. A method for the treatment of depression, comprising administering to a mammal in need thereof an effective amount of a pharmaceutical composition according to claim 26.

30. A method for the treatment of diarrhoea, comprising administering to a mammal in need thereof an effective amount of a pharmaceutical composition according to claim 26.

31. A method for anxiolysis, comprising administering to a mammal in need thereof an effective amount of a pharmaceutical composition according to claim 26.

32. A method for the treatment of urinary incontinence, comprising administering to a mammal in need thereof an effective amount of a pharmaceutical composition according to claim 26.

* * * * *